US010967364B2

(12) United States Patent
Gunnoe et al.

(10) Patent No.: US 10,967,364 B2
(45) Date of Patent: Apr. 6, 2021

(54) CATALYSTS AND METHODS FOR FORMING ALKENYL AND ALKYL SUBSTITUTED ARENES

(71) Applicant: The University of Virginia Patent Foundation, Charlottesville, VA (US)

(72) Inventors: Thomas B. Gunnoe, Palmyra, VA (US); Benjamin Austin Vaughan, Dover, NH (US); Michael S. Webster-Gardiner, Mims, FL (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/561,212

(22) PCT Filed: Mar. 24, 2016

(86) PCT No.: PCT/US2016/023979
§ 371 (c)(1),
(2) Date: Sep. 25, 2017

(87) PCT Pub. No.: WO2016/154416
PCT Pub. Date: Sep. 29, 2016

(65) Prior Publication Data
US 2018/0065116 A1 Mar. 8, 2018

Related U.S. Application Data

(60) Provisional application No. 62/137,853, filed on Mar. 25, 2015.

(51) Int. Cl.
| *C07C 2/66* | (2006.01) |
| *B01J 31/18* | (2006.01) |
| *B01J 31/22* | (2006.01) |
| *B01J 31/00* | (2006.01) |
| *C07C 5/03* | (2006.01) |

(52) U.S. Cl.
CPC .......... *B01J 31/1815* (2013.01); *B01J 31/00* (2013.01); *B01J 31/189* (2013.01); *B01J 31/2226* (2013.01); *B01J 31/2291* (2013.01); *C07C 2/66* (2013.01); *C07C 5/03* (2013.01); *B01J 2231/46* (2013.01); *B01J 2531/0244* (2013.01);
(Continued)

(58) Field of Classification Search
None
See application file for complete search history.

(56) References Cited

U.S. PATENT DOCUMENTS 4,263,212 A * 4/1981 Hong ................. C07C 2/76
548/517
6,127,590 A * 10/2000 Taube .................. C07B 37/00
585/435

FOREIGN PATENT DOCUMENTS

| CN | 103721740 A | 4/2014 |
| WO | WO 03/095084 | * 11/2003 |

OTHER PUBLICATIONS

International Search Report for PCT/US2016/023979 dated Aug. 30, 2016.
(Continued)

*Primary Examiner* — Yun Qian
(74) *Attorney, Agent, or Firm* — Thomas|Horstemeyer, LLP

(57) ABSTRACT

Embodiments of the present disclosure provide for Rh(I) catalysts, methods of making alkenyl substituted arenes (e.g., allyl arene, vinyl arene, and the like), methods of making alkyl substituted arenes, and the like.

11 Claims, 8 Drawing Sheets

(52) U.S. Cl.
CPC ...... *B01J 2531/822* (2013.01); *B01J 2540/22* (2013.01); *B01J 2540/225* (2013.01)

(56) References Cited

OTHER PUBLICATIONS

Webster-Gardiner, Michael S., et al. "Arene C—H activation using Rh (I) catalysts supported by bidentate nitrogen chelates." Catalysis Science & Technology 5.1 (2015): 96-100.

Vaughan, Benjamin A., et al. "A rhodium catalyst for single-step styrene production from benzene and ethylene." Science 348.6233 (2015): 421-424.

Turlington, Christopher R., et al. "Exploring Oxidation of Half-Sandwich Rhodium Complexes: Oxygen Atom Insertion into the Rhodium—Carbon Bond of κ2-Coordinated 2-Phenylpyridine." Organometallics 33.17 (2014): 4442-4448.

O'Reilly, Matthew E., et al. "Reductive Functionalization of a Rhodium (III)—Methyl Bond in Acidic Media: Key Step in the Electrophilic Functionalization of Methane." Organometallics 33.22 (2014): 6504-6510.

Oberg, Kevin Martin. Rhodium-catalyzed cycloadditions to construct nitrogen heterocycles and progress towards the synthesis of ionomycin. Diss. Colorado State University, 2014.

Kani, Ibrahim, et al. "Homogeneous catalysis in supercritical carbon dioxide with rhodium catalysts tethering fluoroacrylate polymer ligands." Tetrahedron 58.20 (2002): 3923-3928.

Fu, Ross. Iridium and rhodium analogues of the Shilov cycle catalyst; and the investigation and applications of the Reduction-Coupled Oxo Activation (ROA) mechanistic motif towards alkane upgrading. California Institute of Technology, 2014.

\* cited by examiner

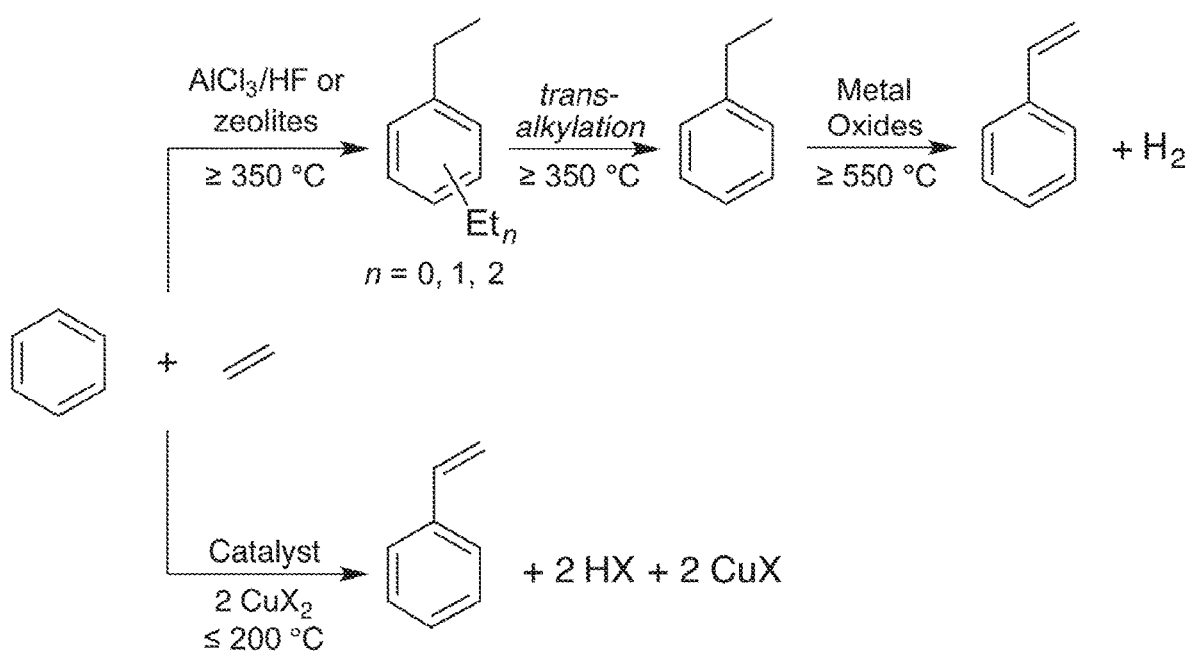
Fig. 1.1

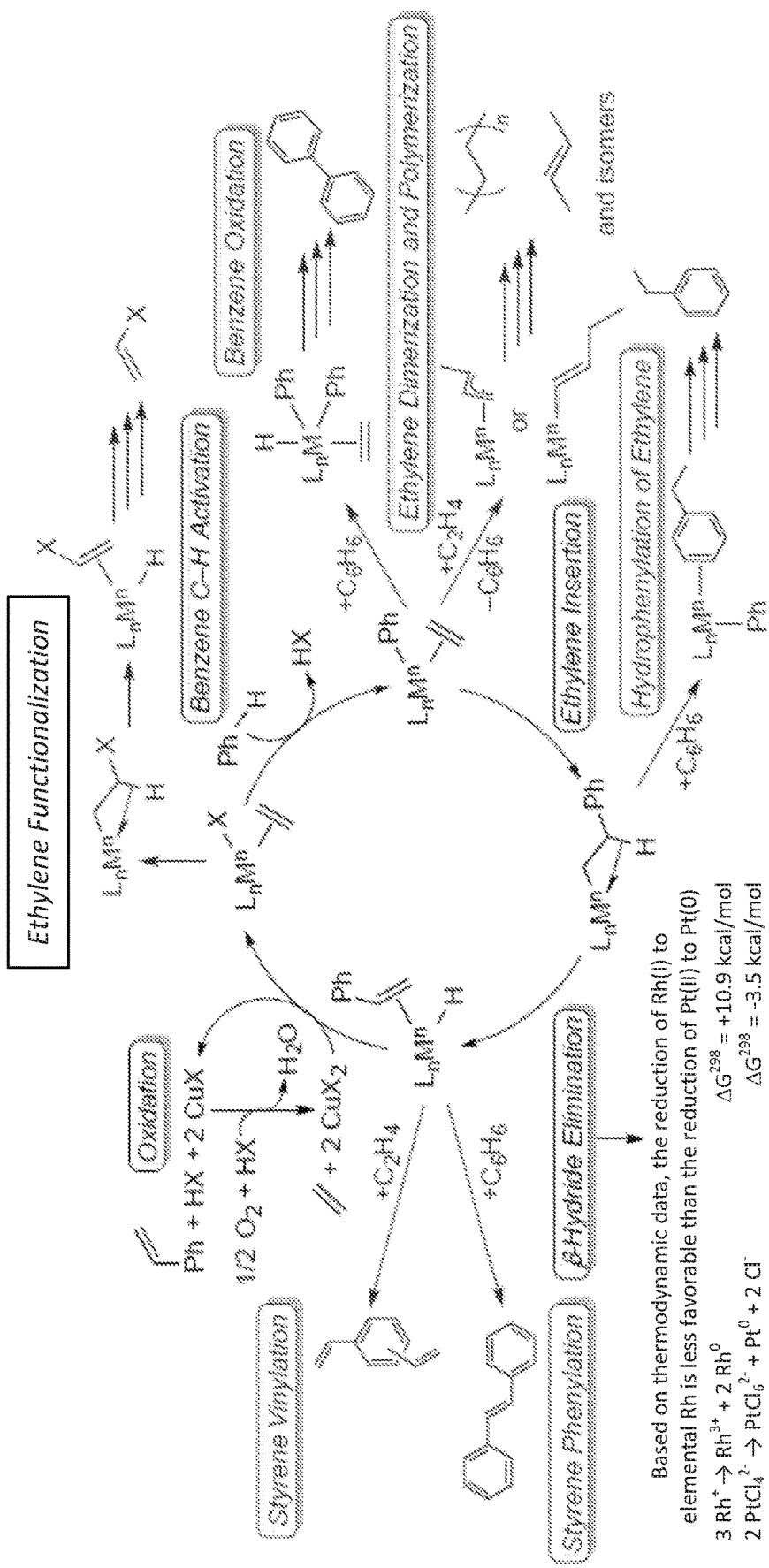
Fig. 1.2

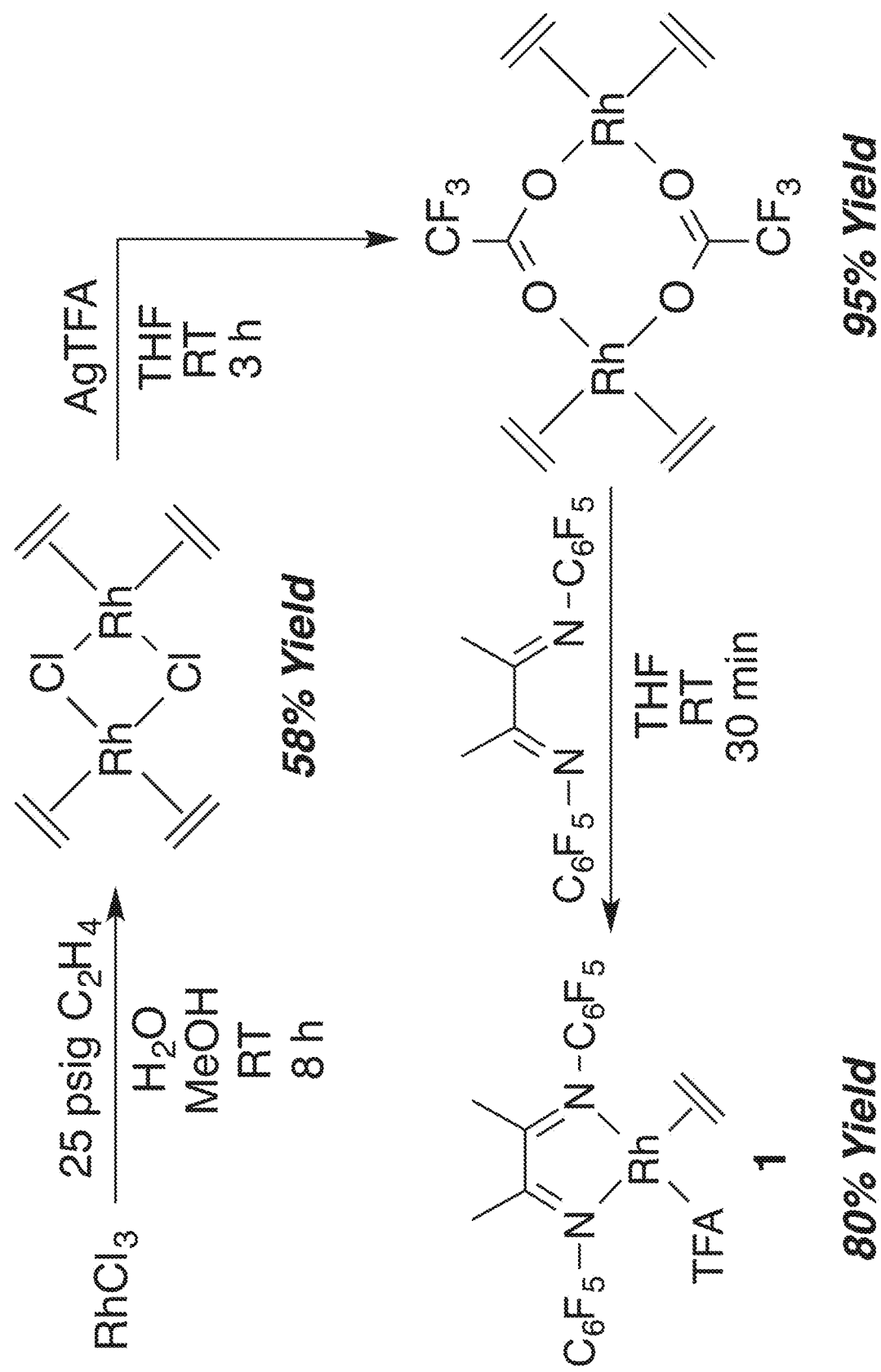
Fig. 1.3

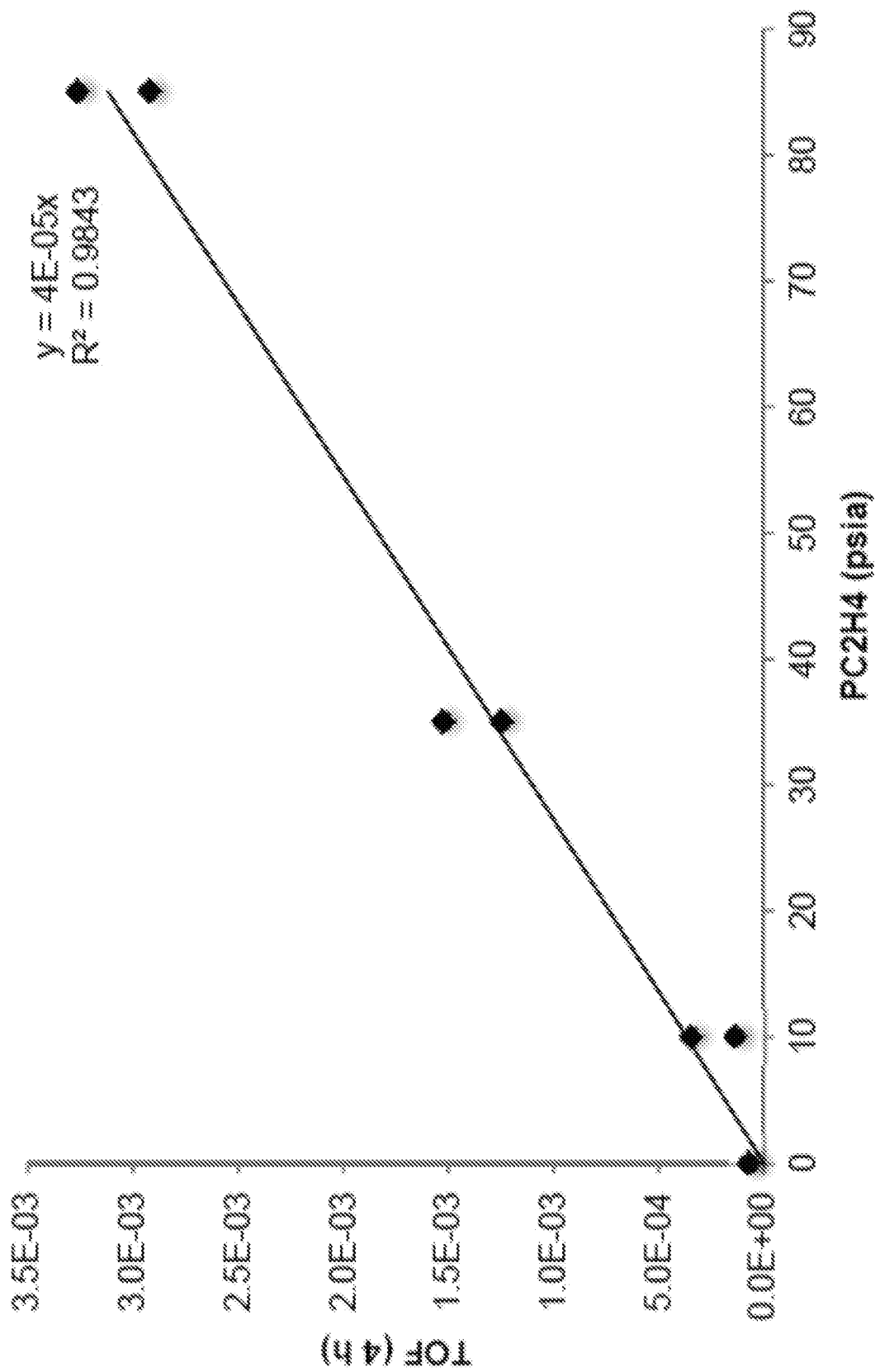
Fig. 1.4

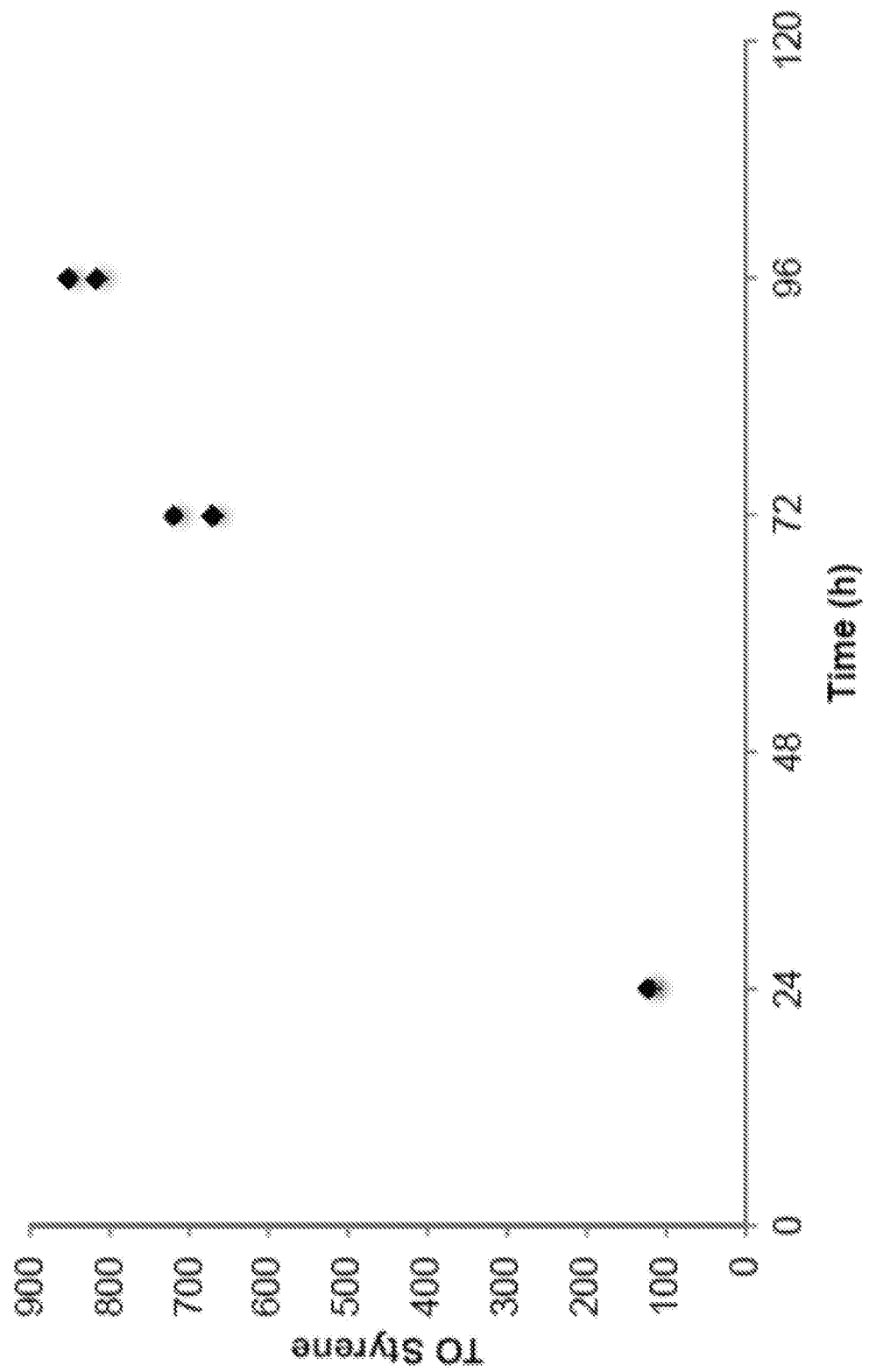
Fig. 1.5

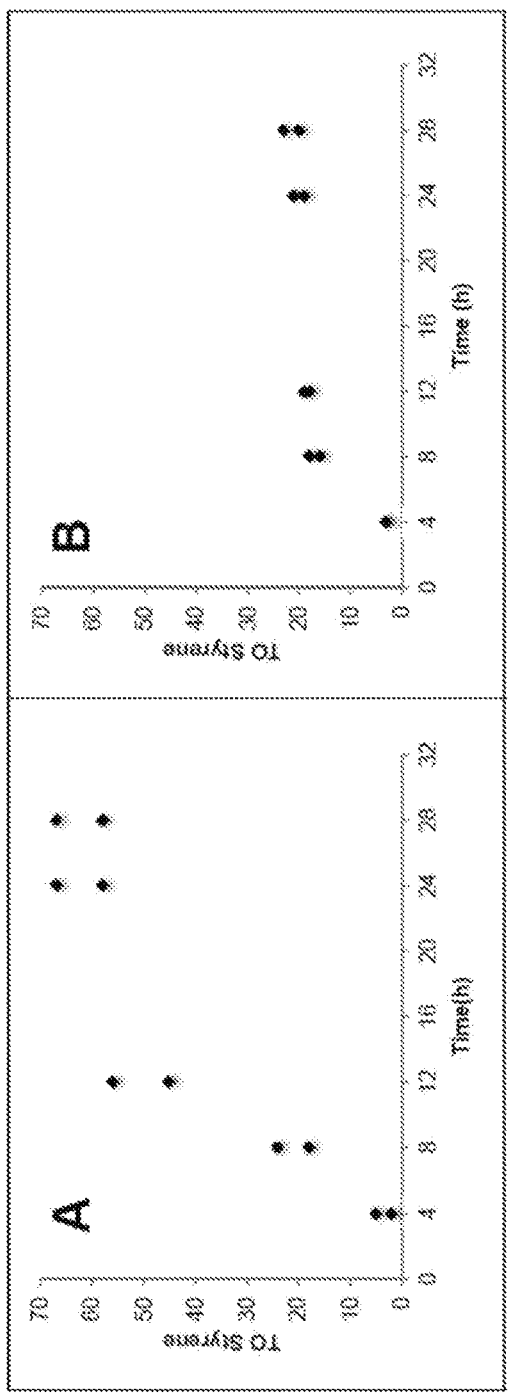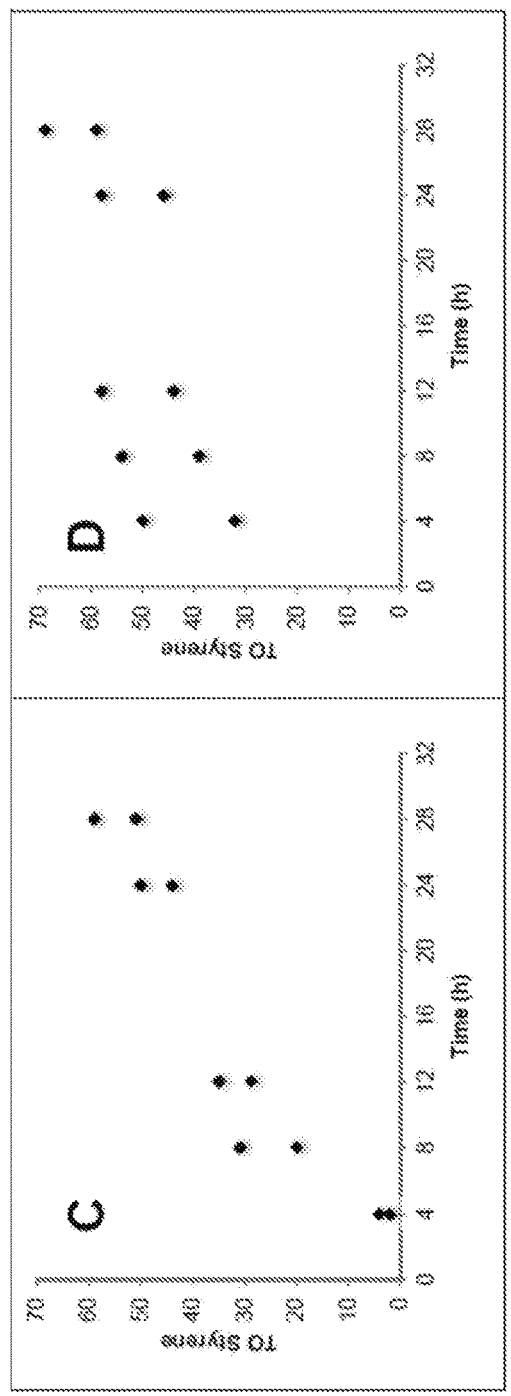

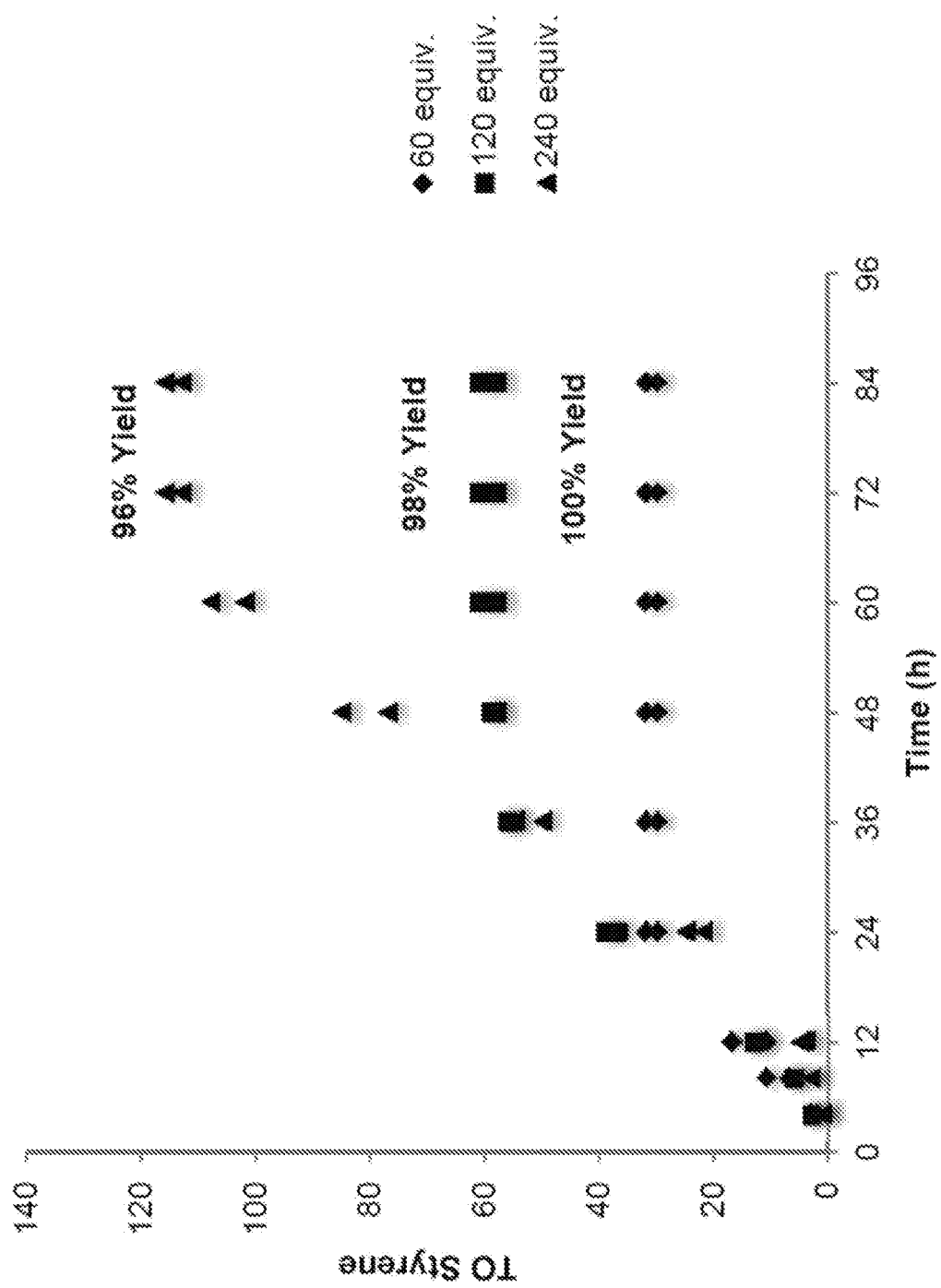
Fig. 1.7

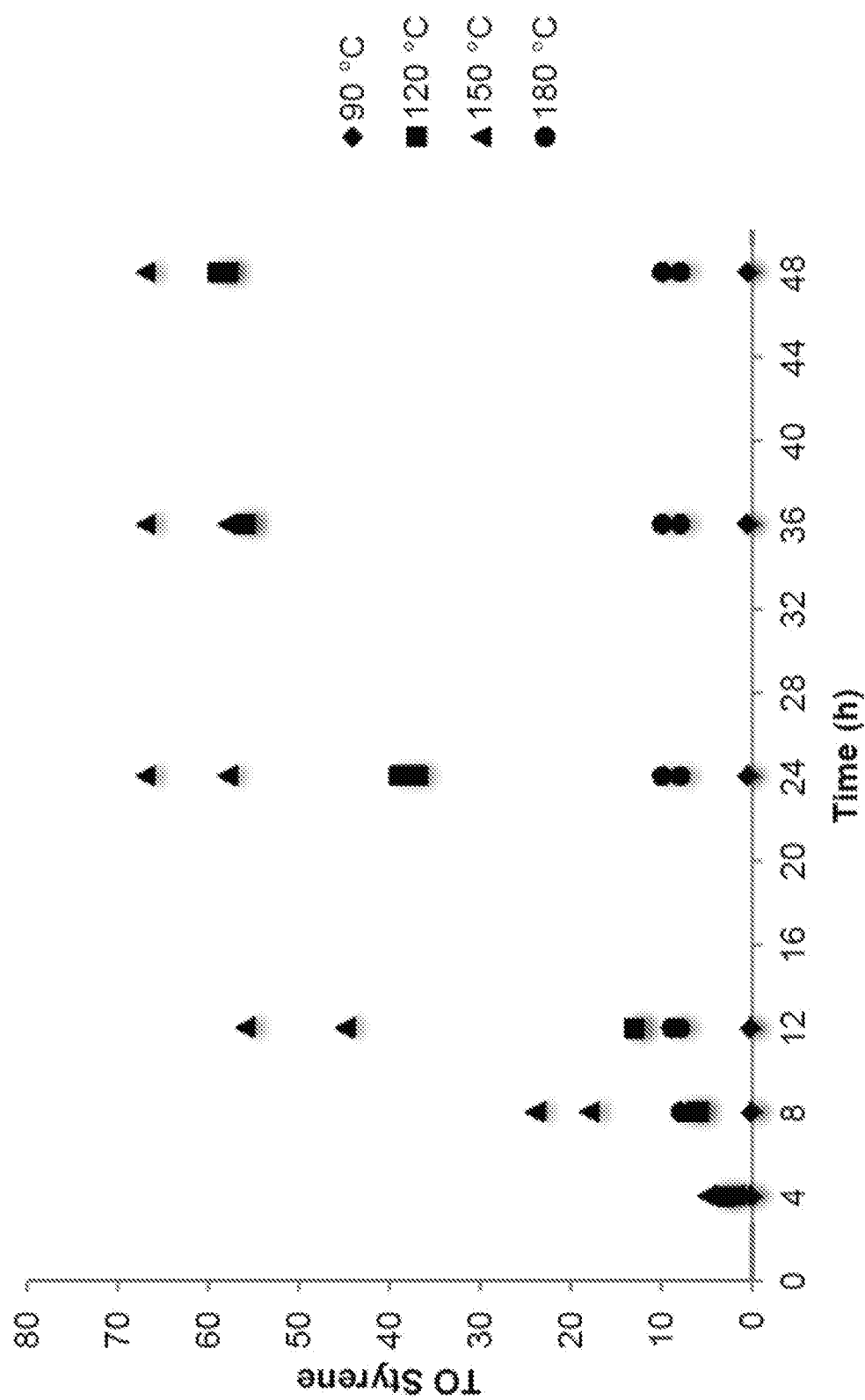
Fig. 1.8

CATALYSTS AND METHODS FOR FORMING ALKENYL AND ALKYL SUBSTITUTED ARENES

CROSS-REFERENCE TO RELATED APPLICATION

This application is the 35 U.S.C. § 371 national stage application of PCT Application No. PCT/US2016/023979, filed Mar. 24, 2016, where the PCT claims priority to U.S. provisional application entitled "COMPOSITIONS AND METHODS FOR SINGLE-STEP STYRENE PRODUCTION" having Ser. No. 62/137,853 filed on Mar. 25, 2015, both of which are herein incorporated by reference in their entireties.

FEDERAL SPONSORSHIP

This invention was made with government support under Grant Nos. DE-SC0000776 and DESC0001298, awarded by The United States Department of Energy. The government has certain rights in the invention.

BACKGROUND

Although a direct process for vinyl arene formation from arenes and olefins offers potential advantages, acid-based (i.e., Friedel-Crafts or zeolite catalysts) catalysis occurs by electrophilic aromatic substitution and does not offer a viable pathway to directly generate vinyl arenes. Transition metal complexes that catalyze olefin hydroarylation by olefin insertion into a metal-aryl bond followed by aromatic C—H activation have been reported as alternatives to acid-based catalysts. For these catalysts, β-hydride elimination from a M-CH$_2$(CH$_2$)$_n$CH$_2$Ar (n=0-10); Ar=aryl) intermediate and dissociation of vinyl arene provides a route for the direct oxidative hydroarylation of olefin. A targeted catalytic cycle exists for the direct oxidative hydroarylation of olefins to produce vinyl arenes, and, since vinyl arenes are easily hydrogenated, a route to alkyl arenes, but despite precedent for the key steps in this catalytic cycle, designing a selective catalyst represents a substantial challenge as many viable and undesirable side reactions are likely to have activation barriers that are similar or lower than the reactions along the desired catalytic cycle. In addition to these possible side reactions, designing a catalyst that achieves high turnover numbers (TON) is difficult since the conditions and the presence of potentially reactive intermediates could be anticipated to result in catalyst decomposition and/or deactivation. Consistent with these challenges, there is no example of a catalyst that achieves the desired results.

SUMMARY

Embodiments of the present disclosure provide for Rh(I) catalysts, methods of making alkenyl substituted arenes (e.g., allyl arene, vinyl arene, and the like), methods of making alkyl substituted arenes, and the like.

An exemplary embodiment of the composition, among others, includes: a rhodium (I) catalyst having one of the following formula: L$_2$Rh(L')X, L$_3$RhX, (L$_1$X$_1$)Rh(L'), [(L)$_2$Rh(μ-X)]$_2$, or (L)$_n$Rh$_m$, wherein L$_2$ is selected from: two independent and neutral first ligands each coordinated to Rh(I) through a carbon donor, nitrogen donor, a phosphorus donor, an oxygen donor, or a sulfur donor, a neutral bidentate ligand coordinated to Rh(I) through either a carbon donor, nitrogen donor, a phosphorus donor, an oxygen donor, or a sulfur donor, or a combination of the neutral first ligand and the neutral bidentate ligand; wherein L' is a neutral second ligand coordinated to Rh(I), wherein X is a mono-anionic group, either coordinated to the metal or not, wherein L$_3$ is a tridentate first ligand coordinated to Rh(I) in a κ$^2$ or κ$^3$ fashion through a carbon donor, a nitrogen donor, a phosphorus donor, an oxygen donor, a sulfur donor, or a combination thereof, wherein L$_1$X$_1$ is a monoanionic bidentate or tridentate second ligand coordinated to Rh(I) in a κ$^2$ or κ$^3$ fashion through a carbon donor, a nitrogen donor, a phosphorus donor, an oxygen donor, a sulfur donor, or a combination thereof, wherein L is a neutral, two-electron donating third ligand coordinated to Rh(I), and wherein m is 1 to 4 and n is 3(m).

An exemplary embodiment of the composition, among others, includes: a rhodium (I) catalyst having the following structure:

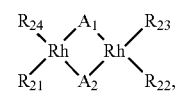

wherein A$_1$ and A$_2$ are independently selected from the group consisting of: a halogen, an acetate group, a sulfur-based ligand, a carbon-based ligand, hydroxyl, alkoxy, oxide, an amido, a phosphide, a phosphido, a nitride, a hydride, a phosphate (PF$_6$), and a borate (BPh$_4$), wherein R$_{21}$, R$_{22}$, R$_{23}$, and R$_{24}$ are independently selected from the group consisting of: an alkyl, an aryl, an acetate, a cyano group, an olefin, an imine, an ether, a nitrile, a ketone, water, a sulfur based ligand, a phosphine, a carbonyl, a phosphite, and a silicon based ligand.

An exemplary embodiment of the composition, among others, includes: a rhodium (I) catalyst having the following structure:

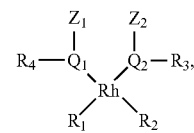

wherein Q$_1$ and Q$_2$ are independently selected from the group consisting of: N, O, P, S, Si, and C, wherein Z$_1$ and Z$_2$ are independently selected from the group consisting of: a halide, an alkyl, an alkenyl, a carbocycle group, a heterocyclo, an aryl, a heteroaryl, an acetate, a nitrile, a phosphite, a carbonyl, and a carboxylate, optionally, Z$_1$ and Z$_2$ are joined together with a bond to form a 5, 6, or 7-membered ring, wherein R$_1$ and R$_2$ are independently selected from the group consisting of: hydrogen, an alkyl, an aryl, an acetate, a cyano group, an olefin, an imine, an ether, a nitrile, a ketone, water, a sulfur based ligand, a phosphine, a carbonyl, a nitrosyl, a silane, and an N-Heterocyclic carbene, wherein R$_3$ and R$_4$ are independently selected from the group consisting of: a halide, an alkyl, an alkenyl, a carbocycle group, a heterocyclo, an aryl, a heteroaryl, an acetate, a cyano group, a nitrile, and a phosphite.

An exemplary embodiment of the composition, among others, includes: a rhodium (I) catalyst having the following structure:

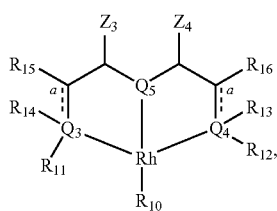

wherein $Q_3$, $Q_4$, and $Q_5$ are independently selected from the group consisting of: N, O, P, S, and Si, wherein $Z_3$ and $Z_4$ are independently selected from the group consisting of: a halide, an alkyl, an alkenyl, a carbocycle group, a heterocyclo, an aryl, a heteroaryl, an acetate, a cyano group, a carbonyl, and a silyl group, optionally, $Z_3$ and $Z_4$ are joined together with a bond to form a 5, 6, or 7-membered ring, wherein $R_{11}$ and $R_{12}$ are independently selected from the group consisting of: hydrogen, an alkyl, an aryl, an acetate, a cyano group, an olefin, an imine, an ether, a nitrile, a ketone, water, a sulfur based ligand, a phosphine, a silyl group, and an N-heterocyclic carbene, wherein $R_{10}$, $R_{13}$, $R_{14}$ $R_{15}$, and $R_{16}$ are independently selected from the group consisting of: a halide, an alkyl, an alkenyl, a carbocycle group, a heterocyclo, an aryl, a heteroaryl, an acetate, a cyano group, a nitrile, and a phosphite wherein, optionally, $R_{15}$ and $R_{14}$, $R_{14}$ and $R_{11}$, or $R_{11}$, $R_{14}$, and $R_{15}$ are joined together with a bond(s) to form a 5, 6, or 7-membered ring, wherein, optionally, $R_{16}$ and $R_{13}$, $R_{13}$ and $R_{12}$, or $R_{12}$, $R_{13}$, and $R_{16}$ are joined together with a bond(s) to form a 5, 6, or 7-membered ring.

An exemplary embodiment of the method, among others, includes:

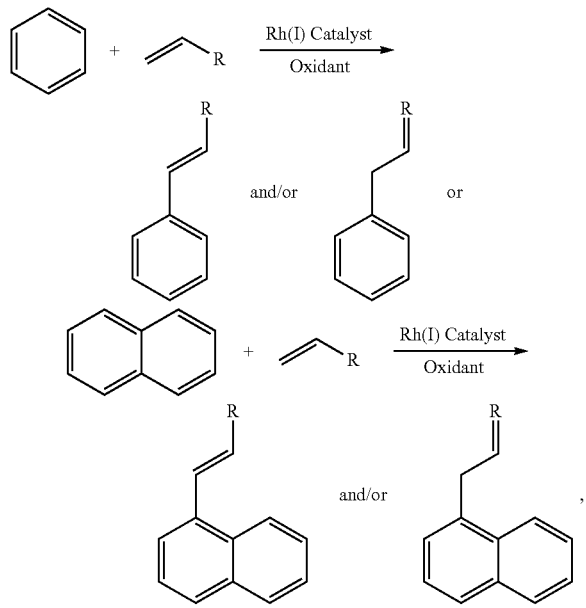

wherein the catalyst is a Rh(I) catalyst as described in any one of claims 1-15, wherein the oxidant is selected from the group consisting of a copper(II) salt, iodates, periodates, nitrogen dioxide, silver salt, peroxide, and a combination thereof, wherein R is selected from the group consisting of: hydrogen, a halide, an alkyl, an alkenyl, a carbocycle group, a heterocyclo, an aryl, and a heteroaryl, wherein, optionally, one or more of the hydrogens on the benzene ring or naphthalene ring is substituted with a group selected from the group consisting of: halogen, a carboxylate, a carbonyl, and an ether.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1 is a comparison of the current route to vinyl arene production (e.g., styrene is used as an example) and the single-step route described herein.

FIG. 1.2 illustrates an exemplary cycle for transition metal-catalyzed vinyl arene production from arene and olefin (e.g., using benzene, ethylene, and styrene as examples) using $CuX_2$ as an oxidant. The cuprous (CuX) product could be recycled back to the cupric state using air or purified oxygen, as shown at the upper left. Some potential side reactions that a selective catalyst must avoid are shown in red.

FIG. 1.3 illustrates the synthesis of a representative catalyst, $(^{FI}DAB)Rh(TFA)(\eta^2\text{-}C_2H_4)$ (1) (RT=room temperature).

FIG. 1.4 illustrates the effect of ethylene pressure on catalysis with $(^{FI}DAB)Rh(TFA)(\eta^2\text{-}C_2H_4)$ (1). Reaction conditions: 0.001 mol % 1, 120 equivalents $Cu(OAc)_2$, 150° C., 4 h. Data for two independent reactions are shown.

FIG. 1.5 illustrates the TO vs. Time plot for catalysis with 0.0001 mol % $(^{FI}DAB)Rh(TFA)(\eta^2\text{-}C_2H_4)$ (1). Reaction conditions: 0.0001 mol % 1, 2400 equiv. $Cu(OAc)_2$, 75 psig $C_2H_4$, 150° C., theoretical maximum TON=1200. Data for two independent reactions are shown (appearance of a single data point indicates overlap of two similar results).

FIGS. 1.6A-D illustrates plots of TO for styrene production vs. time as a function of oxidant using $(^{FI}DAB)Rh(TFA)(\eta^2\text{-}C_2H_4)$ (1). 1.6A) $Cu(OAc)_2$, 1.6B) $Cu(TFA)_2$, 1.6C) $Cu(OPiv)_2$ [OPiv=pivalate], 1.6D) $Cu(OHex)_2$ [OHex=2-ethylhexanoate]. Reaction conditions: 0.001 mol % 1, 25 psig $C_2H_4$, 120 equivalents oxidant, 150° C., theoretical maximum TON=60. Data for two independent reactions are shown for each oxidant type (appearance of a single data point indicates overlap of two similar results).

FIG. 1.7 illustrates the effect of oxidant amount on styrene production using $(^{FI}DAB)Rh(TFA)(\eta^2\text{-}C_2H_4)$ (1). Reaction conditions: 0.001 mol % 1, 25 psig $C_2H_4$, 120° C. Percent yield is reported relative to oxidant, assuming 2 equivalents are required per TO. Data for two independent reactions are shown for each oxidant amount (appearance of a single data point indicates overlap of two similar results).

FIG. 1.8 illustrates the effect of temperature on styrene production using $(^{FI}DAB)Rh(TFA)(\eta^2\text{-}C_2H_4)$ (1). Reaction conditions: 0.001 mol % 1, 120 equivalents $Cu(OAc)_2$, 25 psig $C_2H_4$. Data for two independent reactions are shown for each temperature (appearance of a single data point indicates overlap of two similar results).

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, and the like, which are within the skill of the art. Such techniques are explained fully in the literature.

The following description and examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar or psig. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. Different stereochemistry is also possible, such as products of cis or trans orientation around a carbon-carbon double bond or syn or anti addition could be both possible even if only one is drawn in an embodiment.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions:

By "chemically feasible" is meant a bonding arrangement or a compound where the generally understood rules of organic structure are not violated. The structures disclosed herein, in all of their embodiments are intended to include only "chemically feasible" structures, and any recited structures that are not chemically feasible, for example in a structure shown with variable atoms or groups, are not intended to be disclosed or claimed herein. However, if a bond appears to be intended and needs the removal of a group such as a hydrogen from a carbon, the one of skill would understand that a hydrogen could be removed to form the desired bond.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded. As used herein, the term "optionally substituted" typically refers to from zero to four substituents, wherein the substituents are each independently selected. Each of the independently selected substituents may be the same or different than other substituents. For example, the substituents (e.g., an R type group) of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid, etc. In an embodiment, substituted includes substitution with a halogen.

As used herein, a "derivative" of a compound refers to a chemical compound that may be produced from another compound of similar structure in one or more steps, as in replacement of H by an alkyl, acyl, amino group, etc.

As used herein, "aliphatic" or "aliphatic group" refers to a saturated or unsaturated, linear or branched, cyclic (non-aromatic) or heterocyclic (non-aromatic), hydrocarbon or hydrocarbon group, where each can be substituted or unsubstituted, and encompasses alkyl, alkenyl, and alkynyl groups, and alkanes, alkene, and alkynes, for example, substituted or unsubstituted.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon moiety.

As used herein, "alkyl" or "alkyl group" refers to a saturated aliphatic hydrocarbon, which can be straight or branched, having 1 to 40, 1 to 20, 1 to 10, or 1 to 5 carbon atoms, where the stated range of carbon atoms includes each intervening integer individually, as well as sub-ranges. Examples of alkyl groups include, but are not limited to methyl, ethyl, n-propyl, i-propyl, n-butyl, s-butyl, t-butyl, n-pentyl, and s-pentyl. Reference to "alkyl" or "alkyl group" includes unsubstituted and substituted forms of the hydrocarbon moiety.

As used herein, "alkene" (also referred to as an "olefin") refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethylene, propylene, 1-pentene, 1-hexene, isobutene and the like. Reference to "alkene" includes unsubstituted and substituted forms of the hydrocarbon moiety.

As used herein, "alkenyl" or "alkenyl group" refers to an aliphatic hydrocarbon, which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to "alkyl" or "alkyl group" includes unsubstituted and substituted forms of the hydrocarbon moiety.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon moiety.

As used herein, "alkynyl" or "alkynyl group" refers to straight or branched chain hydrocarbon groups having 2 to 40, 2 to 20, 2 to 10, or 2 to 5 carbon atoms and at least one triple carbon to carbon bond, such as ethynyl. Reference to "alkynyl" or "alkynyl group" includes unsubstituted and substituted forms of the hydrocarbon moiety.

The term "carbocycles" refers to a monocyclic or multicyclic ring system of about 5 to about 40 or about 5 to 34 carbon atoms, preferably of about 6 to about 10 carbon atoms, where the carbocycle can be saturated or unsaturated. In an embodiment, the carbocycle can be aromatic or non-aromatic. In an embodiment, carbocycle can refer to an aryl group. Exemplary carbocycles can refer to functional groups such as phenyl and naphthyl. Reference to carbocycles includes substituted or unsubstituted carbocycles.

As used herein, "aromatic" refers to a monocyclic or multicyclic ring system of 5 to 20 or 5 to 10 carbon atoms having alternating double and single bonds between carbon atoms. Exemplary aromatic groups include benzene, naphthalene, alkyl arene, cyclopentadienyl and the like. Reference to "aromatic" includes unsubstituted and substituted forms of the hydrocarbon moiety.

As used herein, "aryl" or "aryl group" refers to an aromatic monocyclic or multicyclic ring system of 5 to 20 or 5 to 10 carbon atoms. The aryl is optionally substituted with one or more $C_1$-$C_{20}$ alkyl, alkylene, alkoxy, or haloalkyl groups. Exemplary aryl groups include phenyl or naphthyl, or substituted phenyl or substituted naphthyl. Reference to "aryl" or "aryl group" includes unsubstituted and substituted forms of the hydrocarbon moiety.

As used herein, "halo", "halogen", "halide", or "halogen radical" refers to a fluorine, chlorine, bromine, iodine, and astatine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, "cyclic" hydrocarbon refers to any stable 4, 5, 6, 7, 8, 9, 10, 11, or 12 membered, (unless the number of members is otherwise recited), monocyclic, bicyclic, or tricyclic cyclic ring.

As used herein, "heterocycle" refers to any stable 4, 5, 6, 7, 8, 9, 10, 11, or 12 membered, (unless the number of members is otherwise recited), monocyclic, bicyclic, or tricyclic heterocyclic, and the like ring that is saturated or partially unsaturated, and which includes carbon atoms and 1, 2, 3, 4 or more heteroatoms independently selected from the group consisting of N, P, O, and S. If the heterocycle is defined by the number of carbons atoms, then from 1, 2, 3, 4 or more of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The P group may be P, PH, or P-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a heteroatom if the resulting compound is stable. In an embodiment, the heterocycle can include furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, carbazole, thiazole, each of which can be substituted or unsubstituted.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, 4 or more heteroatoms independently selected from the group consisting of N, O, and S. If the heteroaryl is defined by the number of carbons atoms, then 1, 2, 3, 4 or more of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable. In an embodiment, the heteroaryl ring can include furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring).

The term "bicyclic" represents either an unsaturated or saturated stable 7- to 18-membered bridged or fused bicyclic carbon ring. The bicyclic ring may be attached at any atom which affords a stable structure. The term includes, but is not limited to, naphthyl, dicyclohexyl, dicyclohexenyl, and the like.

The term "cyano" refers to a —CN moiety.

The term "nitrile" refers to R'—CN, where R' is selected from an alkyl, an alkenyl, a carbocycle group, a heterocyclo, an aryl, or a heteroaryl.

The term "imine" refers to R'1-N=CR"R'", where R', R", and R'" are each independently selected from an alkyl, an alkenyl, a carbocycle group, a heterocyclo, an aryl, or a heteroaryl.

The term "ether" refers to R'OR", where R' and R" are each independently selected from an alkyl, an alkenyl, a carbocycle group, a heterocyclo, an aryl, or a heteroaryl.

The term "ketone" refers to O=CR'R", where R' and R" are each independently selected from an alkyl, an alkenyl, a carbocycle group, a heterocyclo, an aryl, or a heteroaryl.

The term "phosphine" refers to $PH_3$, or trisubstituted phosphorus atoms such as triphenylphosphine.

The term "sulfur based ligand" refers to R'SR" or R'S or other combinations in which sulfur is incorporated into a ligand, either bound to the metal or not.

The term "silyl" refers to —SiR'R"R'", where R', R", and R'" are each independently selected from an alkyl, an alkenyl, a carbocycle group, a heterocyclo, an aryl, or a heteroaryl.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

General Discussion

Embodiments of the present disclosure provide for Rh(I) catalysts, methods of making alkenyl substituted arenes (e.g., allyl arene, vinyl arene, and the like), methods of making alkyl substituted arenes, and the like. In general, embodiments of the Rh(I) catalyst can be used in a one-step conversion of arenes (e.g., benzene, naphthalene) and olefins to form alkenyl substituted arenes. Embodiments of the present disclosure are advantageous over previously processes for at least one or more of the following: oxidants can be regenerated using oxygen, efficient conversion of the olefin, moderate temperatures (e.g., about 100-250° C.), broad range of pressures for gaseous olefins and broad range of concentrations for liquid or solid olefins, and formation of truly linear (i.e., anti-Markovnikov or straight-chain) alkyl, allyl, and vinyl arenes as the major products. In an embodiment, a catalytic process using a Rh(I) catalyst can convert arenes and olefins to straight-chain alkyl, vinyl or allyl arenes and, hence, through facile hydrogenation of the vinyl or allyl arenes straight-chain alkyl arenes.

In general, embodiments of the present disclosure relate to the oxidative hydroarylation of an olefin (e.g., ethylene) and an arene (e.g., benzene) to form an alkenyl substituted arene (e.g., an allyl or vinyl arene such as styrene) using a Rh(I) catalyst (described below). In an embodiment, the reaction scheme can be represented as one of the following:

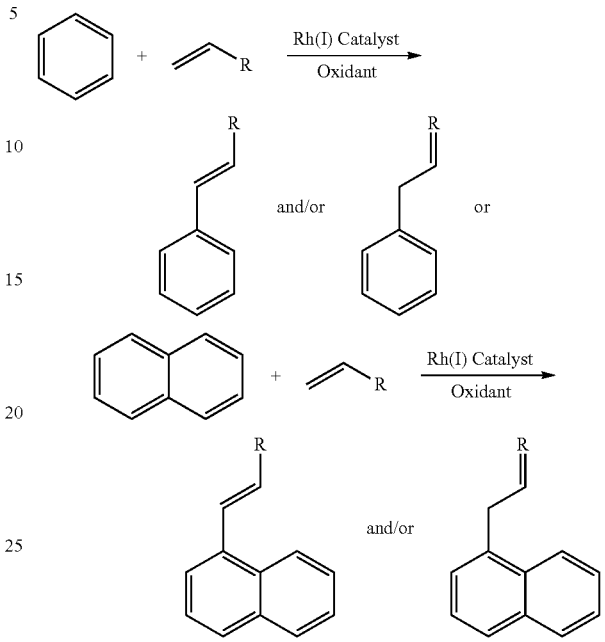

The following scheme illustrates the development of processes that use dioxygen (pure or, ideally, from air) as an additional oxidant. In such an embodiment, the overall reaction produces vinyl or allyl (or isomer) arenes and water (Scheme 3), where dioxygen could be used directly, or indirectly with an in situ oxidant that can be regenerated from dioxygen can be used.

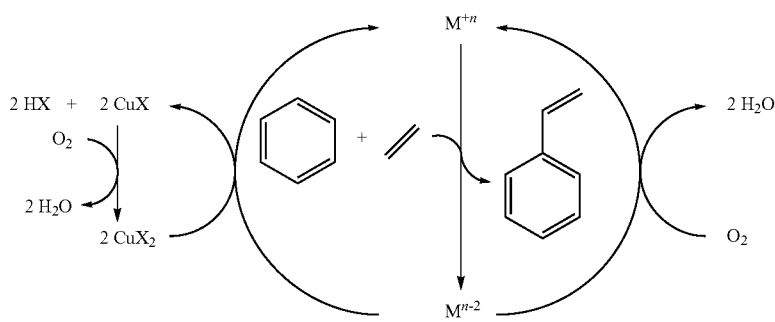

In general, these reactions are very selective for forming the desired product (e.g., linear/straight-chain (anti-Markovnikov) allyl and vinyl arenes), but other products (e.g., branched allyl and vinyl arenes) may be formed as well, typically at lower reaction yields. In an embodiment, the substituted arenes can be produced with about 50, 60, 70, 80, 90, 91, 92, 93, 94, 95, 96, 97, 98, or 99, each up to 100% selectivity (e.g., about 50 to 100%).

In an embodiment, the yield is high relative to oxidant. In one aspect the yield is about 50, 60, 70, 80, or 90, each up to 100% (e.g., about 50 to 100%). In an embodiment, the substituted arene can be produced with 100% selectivity and with a high yield relative to oxidant (≥95%). Additional details about particular reactions are provided in the Examples.

In an embodiment, R can be a group selected from: hydrogen, a halide, an alkyl, an alkenyl, a carbocycle group, a heterocyclo, an aryl, or a heteroaryl. In particular, in the reactant form the R group can be selected so that it produces one of the following: ethylene, propylene, 1-pentene, 1-hexene, isobutylene, vinyl ketones, acrylates, acrylonitriles, etc.

In addition, although benzene and naphthalene are represented above, optionally, one or more of the hydrogens on the benzene ring or naphthalene rings can each be independently substituted with a group such as: halogen, alkyl, alkenyl, allyl, ketone, nitrile, ether, amine, or imine.

In an embodiment, the oxidant can be represented as $A_aX_n$. In an embodiment, "A" can represent an element or combination of elements capable of maintaining a formal positive charge. In an embodiment $A_aX_n$, can be a salt such as a halide salt (e.g., $CuCl_2$). In an embodiment, "A" can be: a transition metal or redox-active main-group metal. In an embodiment, X can be a halide such as chloride, bromide, iodide, an acetate, a trifluoroacetate, a pivalate, and the like. In an embodiment, subscript "a" can represent the oxidation state of "X" and subscript "n" can represent the oxidation state of "A". In an embodiment $A_aX_n$, can be: $CuCl_2$, $CuBr_2$, $Cu(OAc)_2$, $FeCl_3$, $Fe(OAc)_3$, $AgCl$, $MnCl_2$, $IO_3^-$, $IO_4^-$, $NO_2$, $MnCl_3$, etc. In an embodiment, the oxidant can be recyclable using air or purified oxygen. In an embodiment, the air-recyclable oxidant can include a copper(II) salt (e.g., $CuX_2$), iodates, periodates, nitrogen dioxide, iron(III) salts, and the like. These compounds are available for purchase from commercial suppliers, can be prepared from reported procedures, can be prepared in situ by reaction of elements with halogen sources and from natural saline solutions.

In an embodiment, the reaction can be conducted at a temperature of about 100-250° C., while the reaction time can be about 5 mins to 5 days. In an embodiment, the ratio of the arene to olefin can be about 1:100 to 1000:1. In an embodiment the amount of catalyst can be about 20 mol % to 0.000000001 mol %. In an embodiment, the amount of oxidant can be about 2 to 10,000 equivalents relative to catalyst.

In an embodiment, the allyl or vinyl arene can be further processed to form alkyl arenes via hydrogenation. In an embodiment, the hydrogenation reaction scheme can be represented as one of the following:

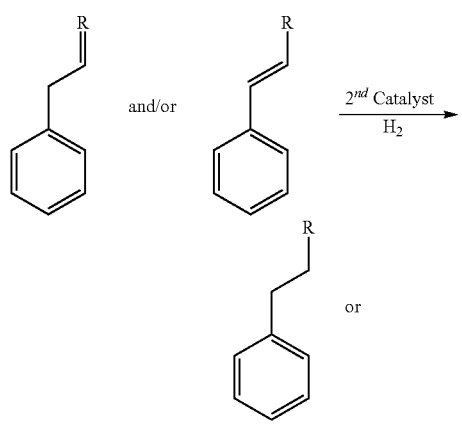

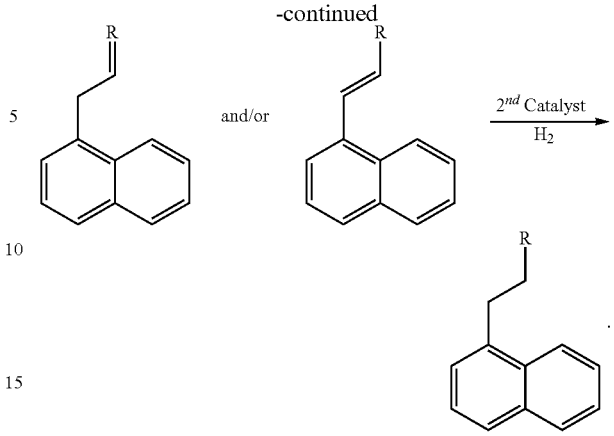

In an embodiment, the reaction can be conducted at a temperature of about 20-250° C., while the reaction time can be about 30 mins to 72 hours in the presence of $H_2$. In an embodiment, the $2^{nd}$ catalyst can include: Pt/C, Pd/C, Raney Ni, Wilkinson's Catalyst, and $PtO_2$. In an embodiment the amount of catalyst can be about 0.00001-50 mol %. In an embodiment, the amount of $H_2$ can be about 15 to 1000 psi.

In an embodiment, the Rh(I) catalyst can have one of the following formula: $L_2Rh(L')X$, $L_3RhX$, $(L_1X_1)Rh(L')$, $[(L)_2Rh(\mu-X)]_2$, or $(L)_nRh_m$.

In an embodiment, $L_2$ can be selected from: a) two independent and neutral first ligands coordinated to Rh(I) through a carbon donor, a nitrogen donor, a phosphorus donor, an oxygen donor, a sulfur donor, or combination of these donors, b) a neutral bidentate ligand coordinated to Rh(I) through a nitrogen donor, a phosphorus donor, an oxygen donor, a sulfur donor, or combination of these donors, or c) a combination of the neutral ligand and the neutral bidentate ligand.

In an embodiment, when $L_2$ is selected from two independent and neutral ligands coordinated to the Rh(I), the neutral ligands can include: an amine (e.g., ammonia, aniline, triethylamine) a pyridine (e.g., pyridine or a substituted pyridine such as 4-methylpyridine), a phosphine (e.g., trimethylphosphine, triphenylphosphine), a phosphite (e.g., trimethylphosphite or triphenylphosphite), other phosphine-based ligands (e.g., phospholes, cyclic phosphites, N-heterocyclic phospheniums, phosphine oxides), an ether (e.g., diethyl ether, dipheny ether, methyl ethyl ether), a ketone or aldehyde (e.g., acetone, benzaldehyde), and an imine.

In an embodiment, when the $L_2$ is the neutral bidentate ligand coordinated to the Rh(I), the neutral bidentate ligand can include: a bipyridine (e.g., 2,2'-bipyridyl), a diamine (e.g. 1,2-diaminopropane, phenylenediamine), a bipyrimidine (e.g. 2,2'-bipyrimidine, 5,5'-bipyrimidine), a bisoxazoline (e.g. BOX, PyBOX), a diphosphine (e.g. 1,2-bis(dimethylphosphino)ethane, 1,2-bis(diphenylphosphino)ethane), a phosphinamine (e.g. DavePhos), a phoshinimine (e.g., (2-phosphanylphenyl)methanimine), an imidate (e.g. ethyl benzimidate, N-Methylbenzamide), a bispyrazole (e.g. 1,1'-bipyrazole, bispyrazoleborate), and a bisimidazole (e.g. 2,2'-bis(4,5-dimethylimidazole), 1,2-bis(imidazole-1-yl)ethane).

In an embodiment, L' can be a neutral second ligand coordinated to Rh(I). In an embodiment, the neutral second ligand can include: an olefin (e.g., ethene, propylene), an imine (e.g. N,1,1-triphenylmethanimine), an ether (e.g., diethyl ether, diphenyl ether, methyl ethyl ether), a nitrile (e.g., acetonitrile, benzonitrile), a ketone or aldehyde (e.g., acetone, benzaldehyde), water, a sulfur based ligand (e.g., dimethylsulfide), and a phosphine (e.g., trimethylphosphine, triphenylphosphine).

In an embodiment, X can be a mono-anionic group, either coordinated to the metal or not. In an embodiment, the mono-anionic group can be: a halide, an alkyl, an alkenyl, a carbocycle group, a heterocyclo, an aryl, a heteroaryl, and an acetate.

In an embodiment, $L_3$ can be a tridentate first ligand coordinated to Rh(I) in a $\kappa^2$ or $\kappa^3$ fashion through a carbon donor, a nitrogen donor, a phosphorus donor, an oxygen donor, a sulfur donor, or a combination thereof. In an embodiment, the tridentate first ligand can be: a terpyridine, a pyridyl diimine, a triphosphine, a diphosphine imine, a bis(phosphino)pyridine, a tris(pyrazolyl)alkane, a tris(ethylenediamine), a trithiolate, a trithiolene, a bis(imino)furan, and the like.

In an embodiment, $L_1X_1$ can be a monoanionic bidentate or tridentate second ligand coordinated to Rh(I) in a $\kappa^2$ or $\kappa^3$ fashion through a carbon donor, a nitrogen donor, a phosphorus donor, an oxygen donor, a sulfur donor, or a combination thereof. In an embodiment, the monoanionic bidentate or tridentate second ligand, can be: diphosphino aryl, imidates, diketiminates, trispyrazolylborate, trisimidazoles, pyridine aryl imidazoles, tris(pyrazolyl)borates, and the like.

In an embodiment, L can be a neutral, two-electron donating third ligand coordinated to Rh(I). In an embodiment, the neutral third ligand is selected from the group consisting of: an olefin, an imine, an ether, a nitrile, a ketone, water, a sulfur based ligand, a phosphine, a phosphine-based ligand, an N-heterocyclic carbene.

In an embodiment, m can be 1 to 4 and n is 3(m) (e.g., 3, 6, 9, 12).

In an embodiment and in addition to those described above, the Rh(I) catalyst can have the following formula:

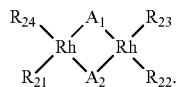

In an embodiment, $A_1$ and $A_2$ can each be independently selected from: a halogen, an acetate group, a sulfur-based ligand, a carbon-based ligand (e.g., alkyl, carbene, carbonyl), hydroxyl or alkyoxy, oxide or bridging ligands based on nitrogen, phosphorus or hydrogen (e.g., amido, phosphide, phosphido, nitride, hydride). In an embodiment, $R_{21}$, $R_{22}$, $R_{23}$, or $R_{24}$ can each be independently selected from: an alkyl, an aryl, an acetate, a cyano group, an olefin, an imine, an ether, a nitrile, a ketone, water, a sulfur based ligand, a phosphine, an N-heterocyclic carbene, or other neutral ligands. In an embodiment, the Rh(I) catalyst can be:

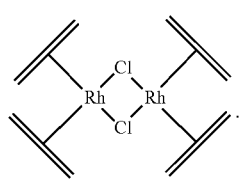

In an embodiment, the Rh(I) catalyst can have the following structure:

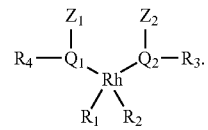

In an embodiment, $Q_1$ and $Q_2$ can be independently selected from: N, O, P, S, C, or Si. In an embodiment, $Z_1$ and $Z_2$ can be independently selected from: a halide, an alkyl, an alkenyl, a carbocycle group, a heterocycle, an aryl, a heteroaryl, an acetate, or related substituents (e.g., carboxylates, amines, phosphides, nitrogen-based, phosphorous-based, silicon-based). Optionally, $Z_1$ and $Z_2$ can joined together with a bond to form a 4, 5, 6, 7, 8 or 9-membered ring.

In an embodiment, $R_1$ and $R_2$ can be independently selected from: a radical group such as hydrogen, an alkyl, an aryl, an acetate, or a cyano group, or a neutral group such as an olefin, an imine, an ether, a nitrile, a ketone, water, a sulfur based ligand, a phosphine, N-heterocyclic carbene, or other neutral ligand (e.g., heteroaryl, amines). In an embodiment, $R_3$ and $R_4$ can be independently selected from: a halide, an alkyl, an alkenyl, a carbocycle group, a heterocycle, an aryl, a heteroaryl, an acetate, a cyano group, and other related substituent (e.g., phosphorus- and/or sulfur-based substituents).

In an embodiment, the Rh(I) catalyst can have the following structure:

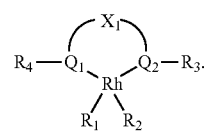

In an embodiment, $X_1$ can be selected from: —$(CR_{5(2)})_q$—, =$(CR_5)_r$—, =$(CR_5CR_{6(2)})_s$—, =$CR_5CR_6$=, and the like. In an embodiment, $R_5$ and $R_6$ can be independently selected from: hydrogen, a halide, an alkyl, an alkenyl, a carbocycle group, a heterocyclo, an aryl, a heteroaryl, an acetate, a cyano group, or related substituent. In an embodiment, each of q, r, and s are independently selected from 1 to 6.

In an embodiment, the Rh(I) catalyst can have the following structure:

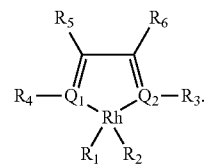

In an embodiment, the Rh(I) catalyst can be one of the following:

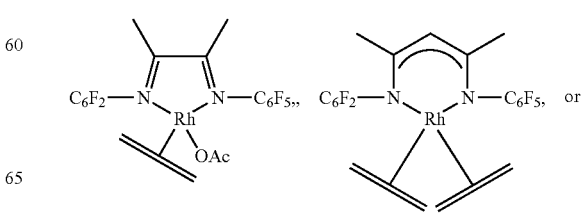

-continued

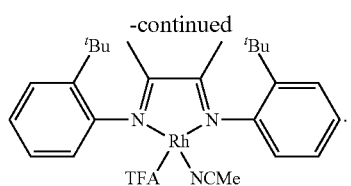

In an embodiment, the Rh(I) catalyst can have the following formula:

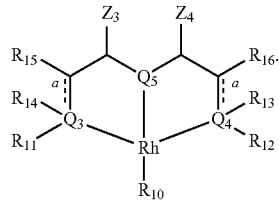

In an embodiment, $Q_3$, $Q_4$, and $Q_5$ can be independently selected from: N, O, P, S, C or Si. In an embodiment, $Z_3$ and $Z_4$ can be independently selected from: a halide, an alkyl, an alkenyl, a carbocycle group, a heterocyclo, an aryl, a heteroaryl, an acetate, a cyano group, or related substituent. In an embodiment, optionally, $Z_3$ and $Z_4$ can joined together with a bond to form a 5, 6, or 7-membered ring. "a" on the rings indicates that the bond can be a single or double bond depending upon $Q_3$ and $Q_4$.

In an embodiment, $R_{12}$ and $R_{12}$ can be independently selected from: a radical such as hydrogen, an alkyl, an aryl, an acetate, or a cyano group, or a neutral moiety such as an olefin, an imine, an ether, a nitrile, a ketone, water, a sulfur based ligand, a phosphine, an N-heterocyclic carbene, or other neutral ligand. In an embodiment, $R_{10}$, $R_{13}$, $R_{14}$ $R_{15}$, and $R_{16}$ can each be independently selected from: a halide, an alkyl, an alkenyl, a carbocycle group, a heterocyclo, an aryl, a heteroaryl, an acetate, a cyano group, or related substituent. In an embodiment, optionally, $R_{15}$ and $R_{14}$, or $R_{14}$, or $R_{11}$, or $R_{11}$, $R_{14}$, and $R_{15}$ can be joined together with a bond(s) to form a 5, 6, or 7-membered ring. In an embodiment, optionally, $R_{16}$ and $R_{13}$, or $R_{13}$ and $R_{12}$, or $R_{12}$, $R_{13}$, and $R_{16}$ can be joined together with a bond(s) to form a 5, 6, or 7-membered ring.

In an embodiment, the Rh(I) catalyst can have the following formula:

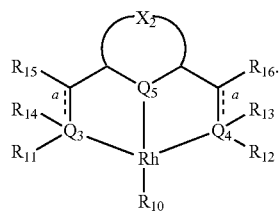

In an embodiment, $X_2$ can be selected from: —$(CR_{5(2)})_q$—, =$(CR_5)_r$—, =$(CR_5CR_{6(2)})_s$—, =$CR_5CR_6$=, and the like. In an embodiment $R_5$ and $R_6$ can each be independently selected from: hydrogen, a halide, an alkyl, an alkenyl, a carbocycle group, a heterocyclo, an aryl, a heteroaryl, an acetate, a pivalate, a hexanoate, and the like. In an embodiment, each of Q, R, and S can be independently selected from 1 to 6. "a" on the rings indicates that the bond can be a single or double bond depending upon $Q_3$ and $Q_4$.

In an embodiment, the Rh(I) catalyst can have the following formula:

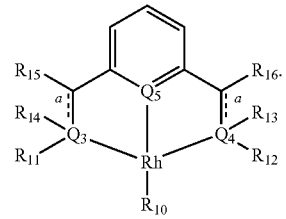

In an embodiment, the Rh(I) catalyst can include:

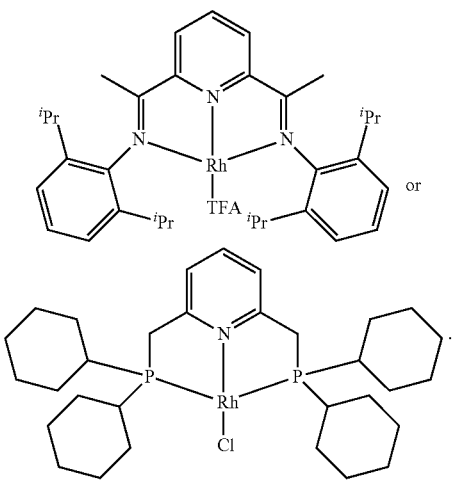

Additional details about the catalysts are provided in the Examples.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Rising global demand for fossil resources has prompted a renewed interest in catalyst technologies that increase the efficiency of conversion of hydrocarbons from petroleum and natural gas to higher value materials. Styrene is currently produced from benzene and ethylene through the intermediacy of ethylbenzene, which must be dehydrogenated in a separate step. The direct oxidative conversion of benzene and ethylene to styrene could provide a more efficient route, but achieving high selectivity and yield for this reaction has been challenging. Here we report that the Rh catalyst $(^{F7}DAB)Rh(TFA)(\eta^2-C_2H_4)$ [$^{F7}DAB$=N,N'-bis(pentafluorophenyl)-2,3-dimethyl-1,4-diaza-1,3-butadiene;

TFA=trifluoroacetate] converts benzene, ethylene and Cu(II) acetate to styrene, Cu(I) acetate, and acetic acid with 100% selectivity and yields ≥95%. Turnover numbers>800 have been demonstrated with catalyst stability up to 96 hours.

Vinyl arenes are important precursors for fine chemical synthesis as well as for the preparation of plastics and elastomers.(1-5) For example, styrene is produced globally on a scale of ~18.5 million tons.(2) Current methods for the large-scale production of vinyl arenes involve multiple steps, typically beginning with arene alkylation using a Friedel-Crafts (e.g., $AlCl_3$ with HF) or zeolite catalyst followed by energy-intensive dehydrogenation of the alkyl group (FIG. 1.1).(1-6) Friedel-Crafts catalysis suffers from the use of harsh acids, including HF, low selectivity for the mono-alkylated product (poly-alkylation is inherent to the mechanism), and the generation of stoichiometric waste.(2) Zeolite catalysts have improved the process for benzene alkylation, yet these catalysts still require high temperatures (generally 350 to 450° C.) and give poly-alkylated products. (2, 7-10)

An alternative method for the production of vinyl arenes is a direct and single-step oxidative arene vinylation (FIG. 1.1). If the terminal oxidant is oxygen from air (either introduced in situ or used to recycle a different in situ oxidant), the net reaction is the conversion of benzene, ethylene and oxidant to styrene and water, or, more generally, arene, olefin and oxidation to vinyl or allyl arene).(11) Acid-based (i.e., Friedel-Crafts or zeolite catalysts) catalysis occurs by electrophilic aromatic substitution and does not offer a viable pathway to directly generate vinyl arenes. Transition metal complexes that catalyze ethylene hydrophenylation by benzene C—H activation followed by ethylene insertion into a metal-phenyl bond have been reported as alternatives to acid-based catalysts (FIG. 1.2).(12-25) For these catalysts, β-hydride elimination from a M-$CH_2CH_2Ph$ intermediate and dissociation of styrene provides a route for the direct oxidative vinylation of benzene (FIG. 1.2).

Previously, the use of platinum(II) catalysts for the hydrophenylation of ethylene to produce ethylbenzene has been studied.(16-19, 26-28) Through a combination of experimental and computational mechanistic studies, it was discerned that a competing β-hydride elimination pathway from Pt—$CH_2CH_2Ph$ intermediates to form a Pt-styrene hydride complex, which can lead to the formation of free styrene.(28) Here, the formation of styrene also results in catalyst decomposition.(27) The thermodynamic driving force for the formation of Pt presents a substantial challenge to achieving long-lived vinyl arene production with these catalysts.(11)

FIG. 1.2 shows a targeted catalytic cycle for the direct oxidative vinylation of benzene to produce styrene. Despite precedent for the key steps in this catalytic cycle, designing a selective catalyst represents a substantial challenge as many competing side reactions (shown in red) are likely to have activation barriers that are similar to or lower than those of the reactions along the desired catalytic cycle. In addition to these possible side reactions, designing a molecular catalyst that achieves high turnover numbers (TON) is difficult because the oxidative conditions and the presence of potentially reactive metal-hydride intermediates could be anticipated to result in catalyst decomposition.

Table 1 compares previously reported homogeneous catalysts for direct oxidative styrene synthesis from ethylene and benzene.(29-34) Generally, all suffer from one or more of the following drawbacks: low selectivity, low yield, low TON, and/or use of oxidants that cannot be regenerated using oxygen. Herein, a rhodium catalyst for the selective one-step production of styrene from benzene, ethylene and Cu(II) salts is reported. A Cu(II) salt is particularly attractive as the in situ oxidant because of industrial precedent for recycling reduced Cu(I) using oxygen or air. In the commercial Wacker-Hoechst process for ethylene oxidation,(35, 36) use of oxygen or air to reoxidize Cu(I) to Cu(II) has proven viable both in situ as well as in a second step.(37)

TABLE 1

Comparison of previously reported catalysts for styrene production. TON = Turnover number for styrene. Selectivity is defined as turnovers styrene/total turnovers (all products), and is given as a percentage. Yield of styrene is reported relative to the limiting reagent.

| Catalyst | Oxidant | TON | Selectivity | Yield |
|---|---|---|---|---|
| $Rh_4(CO)_{12}$[*] | $C_2H_4$/CO | 472 | 37% | 19% |
| $(acac)_2Rh(Cl)(H_2O)$[†] | $Cu(OAc)_2$ | 24 | 89% | 36% |
| $Rh(PMe_3)_2(CO)(Cl)$[‡] | hv | 3 | 38% | 18% |
| $Pd(OAc)_2$[§] | AgOAc | 0.59 | 44% | 12% |
| $Pd(OAc)_2$[∥] | $Cu(OAc)_2/O_2$ | 19 | 29% | 5% |
| $(DBM)Pd(OAc)_2$[¶] | HPA[‡‡] | 100 | 58% | 2% |
| $(3,5-DCP)Pd(OAc)_2$[#] | $PhCO_3{}^tBu$ | 6.6 | 100% | 33% |
| $(^{F7}DAB)Rh(TFA)(C_2H_4)$[**] | $Cu(OAc)_2$ | 115 | 100% | 96% |
| $(^{F7}DAB)Rh(TFA)(C_2H_4)$[††] | $Cu(OAc)_2$ | 835 | 100% | 70% |

[*] Reference(29).
[†] Reference(30), acac = acetylacetonate.
[‡] Reference(34).
[§] Reference(31).
[∥] Reference(30).
[¶] Reference(32), DBM =dibenzoylmethane.
[#] Reference(33), DCP = 3,5-dichloropyridine.
[**] $^{F7}$DAB = N,N'-bis(pentafluorophenyl)-2,3-dimethyl-1,4-diaza-1,3-butadiene; TFA = trifluoroacetate; 0.001 mol % catalyst loading; described herein.
[††] $^{F7}$DAB = N,N'-bis(pentafluorophenyl)-2,3-dimethyl-1,4-diaza-1,3-butadiene; TFA = trifluoroacetate; 0.0001 mol % catalyst loading; described herein.
[‡‡] HPA = $H_3PMo_{12}O_{40}\cdot 30H_2O$.

FIG. 1.3 illustrates the synthesis of a representative catalyst, $(^{F7}DAB)Rh(TFA)(\eta^2-C_2H_4)$ (1) (RT=room temperature). Heating a 20 mL benzene solution of $(^{F7}DAB)Rh(TFA)(\eta^2-C_2H_4)$ (1) (0.001 mol % relative to benzene) with ethylene and $Cu(OAc)_2$ (120 equivalents relative to 1) to 150° C. affords 58/62 turnovers (TO) of styrene after 24 h (for all TOs reported, two runs were performed, and both results are given). Aliquots of the reaction mixture were analyzed by GC/FID using relative peak areas versus an internal standard (decane). This corresponds to quantitative yield based on the Cu(II) limiting reagent. The calculated yield here assumes two equivalents of Cu(II) are consumed to produce two equivalents of Cu(I) per equivalent of styrene. No other products were observed upon analysis of the reaction mixture by GC/MS or GC/FID, indicating high selectivity for styrene production. Detection limits for the instruments were equivalent to ~1 TO of product. Specifically, we looked for evidence of stilbene, biphenyl, and vinyl acetate production, as these are the most commonly observed byproducts in previously reported catalysis (Table 1).

With a competent catalyst in hand, we next sought to optimize reaction conditions. The effect of oxidant properties on catalysis with 1 was the first parameter investigated. Both soluble (copper 2-ethylhexanoate [$Cu(OHex)_2$] and copper pivalate [$Cu(OPiv)_2$]) and insoluble (copper acetate [$Cu(OAc)_2$] and copper trifluoroacetate hydrate [$Cu(TFA)_2$]) Cu(II) salts were screened. FIG. 1.5 shows a plot of turnovers versus time for the various Cu(II) oxidants. Using a turnover frequency (TOF) calculated after 4 hours of reaction, soluble $Cu(OHex)_2$ gives the fastest initial rate with a TOF of $2.8 \times 10^{-3}$ s$^{-1}$, but the reaction does not reach 100% yield relative to oxidant until 28 h, which may indicate that catalyst deactivation occurs. $Cu(OAc)_2$ affords a slower initial rate than $Cu(OHex)_2$, with a TOF of $2.8 \times 10^{-4}$ s$^{-1}$ after 4 h, but this oxidant provides a more stable catalytic process. Both $Cu(TFA)_2$ and $Cu(OPiv)_2$ afford slower initial rates; reactions with $Cu(OPiv)_2$ reach 92% yield after 28 h, whereas reactions with $Cu(TFA)_2$ produce 19 TO styrene (32% yield) after 20 h.

In order to study catalyst longevity, we varied the amount of $Cu(OAc)_2$. Between 60 and 240 equivalents (relative to 1) the yield of styrene relative to oxidant was always >95% (FIG. 1.7). These near-quantitative yields demonstrate that the catalytic process using 1 as a precursor is stable and long-lived. For a reaction using 0.0001 mol % 1 and 2400 equivalents of $Cu(OAc)_2$, the catalyst remained active over a period of 96 hours and afforded a TON of 817/852. A plot of TO versus time shows that the Rh catalyst is stable through at least 96 hours (FIG. 1.5). Importantly, 1 is tolerant to a large excess of oxidant without any decrease in activity. The effect of temperature on catalysis was also examined (FIG. 1.8). Generally, the rate of reaction increased with temperature. Minimal activity (<1 TO) was also observed at temperatures<100° C. The optimal temperature in this case proved to be 150° C.

The reaction rate also increases with increasing ethylene pressure. To determine the TOF, we measured TO after 4 h of reaction. FIG. 1.4 shows a plot of TOF vs ethylene pressure. A linear correlation is observed. Thus, the reaction rate appears to have a first-order dependence on ethylene concentration, and more rapid rates of reaction are expected at higher olefin concentrations. This is in contrast to previously reported Pt(II) and Ru(II) catalysts for the hydrophenylation of ethylene, which show an inverse dependence on ethylene pressure.(14, 17)

REFERENCES, EXAMPLE 1

1. G. A. Olah, Á. Molnár, *Hydrocarbon Chemistry* (Wiley, Hoboken, N.J., ed. 2, 2003).
2. C. Perego, P. Pollesel, Advances in Aromatics Processing Using Zeolite Catalysts in *Advances in Nanoporous Materials*, E. Stefan, Ed. (Elsevier, Oxford, 2010), vol. 1, pp. 97-149.
3. S.-S. Chen, Styrene in *Kirk-Othmer Encyclopedia of Chemical Technology*. (Wiley, Hoboken, N.J., 2000).
4. H. A. Wittcoff, B. G. Reuben, J. S. Plotkin, Chemicals and Polymers from Ethylene in *Industrial Organic Chemicals*. (Wiley, Hoboken, N.J., 2004), pp. 100-166.
5. Process Evaluation/Research Planning (PERP) Program Report, *Styrene/Ethylbenzene*, (PERP Report 91-9, Chem Systems, Inc., New York, 1992).
6. M. Lucchini, A. Galeotti, "Improved process for the dehydrogenation of alkylaromatic hydrocarbons for the production of vinyl-aromatic monomers" (International Patent WO2007073918A1, 2007).
7. C. Perego, P. Ingallina, Recent advances in the industrial alkylation of aromatics: new catalysts and new processes. *Catal. Today* 73, 3 (2002).
8. C. Perego, P. Ingallina, Combining alkylation and transalkylation for alkylaromatic production. *Green Chem.* 6, 274 (2004).
9. J. Čejka, B. Wichterlová, Acid-Catalyzed Synthesis of Mono- and Dialkyl Benzenes over Zeolites: Active Sites, Zeolite Topology, and Reaction Mechanisms. *Cat. Rev.* 44, 375 (2002).
10. I. M. Gerzeliev, S. N. Khadzhiev, I. E. Sakharova, Ethylbenzene synthesis and benzene transalkylation with diethylbenzenes on zeolite catalysts. *Pet. Chem.* 51, 39 (2011).
11. *CRC handbook of chemistry and physics* (1977).
12. M. Lail, B. N. Arrowood, T. B. Gunnoe, Addition of Arenes to Ethylene and Propene Catalyzed by Ruthenium. *J. Am. Chem. Soc.* 125, 7506 (2003).
13. M. Lail et al., Experimental and Computational Studies of Ruthenium(II)-Catalyzed Addition of Arene C—H Bonds to Olefins. *Organometallics* 23, 5007 (2004).
14. N. A. Foley, J. P. Lee, Z. Ke, T. B. Gunnoe, T. R. Cundari, Ru(II) Catalysts Supported by Hydridotris(pyrazolyl)borate for the Hydroarylation of Olefins: Reaction Scope, Mechanistic Studies, and Guides for the Development of Improved Catalysts. *Acc. Chem. Res.* 42, 585 (2009).
15. E. E. Joslin et al., Catalytic Hydroarylation of Ethylene Using TpRu(L)(NCMe)Ph (L=2,6,7-Trioxa-1-phosphabicyclo[2,2,1]heptane): Comparison to TpRu(L')(NCMe)Ph Systems (L'=CO, $PMe_3$, $P(pyr)_3$, or $P(OCH_2)_3CEt$). *Organometallics* 31, 6851 (2012).
16. J. R. Andreatta, B. A. McKeown, T. B. Gunnoe, Transition metal catalyzed hydroarylation of olefins using unactivated substrates: Recent developments and challenges. *J. Organomet. Chem.* 696, 305 (2011).
17. B. A. McKeown et al., Mechanistic Studies of Ethylene Hydrophenylation Catalyzed by Bipyridyl Pt(II) Complexes. *J. Am. Chem. Soc.* 133, 19131 (2011).
18. B. A. McKeown, H. E. Gonzalez, T. B. Gunnoe, T. R. Cundari, M. Sabat, $Pt^{II}$-Catalyzed Ethylene Hydrophenylation: Influence of Dipyridyl Chelate Ring Size on Catalyst Activity and Longevity. *ACS Catal.* 3, 1165 (2013).
19. B. A. McKeown, B. M. Prince, Z. Ramiro, T. B. Gunnoe, T. R. Cundari, $Pt^{II}$-Catalyzed Hydrophenylation of α-Olefins: Variation of Linear/Branched Products as a Function of Ligand Donor Ability. *ACS Catal.* 4, 1607 (2014).
20. S. A. Burgess et al., Hydrophenylation of ethylene using a cationic Ru(II) catalyst: comparison to a neutral Ru(II) catalyst. *Chem. Sci.* 5, 4355 (2014).
21. W. D. Jones, J. A. Maguire, G. P. Rosini, Thermal and photochemical substitution reactions of $CpRe(PPh_3)_2H_2$ and $CpRe(PPh_3)H_4$. Catalytic insertion of ethylene into the C—H bond of benzene. *Inorg. Chim. Acta* 270, 77 (1998).
22. A. T. Luedtke, K. I. Goldberg, Intermolecular Hydroarylation of Unactivated Olefins Catalyzed by Homogeneous Platinum Complexes. *Angew. Chem., Int. Ed.* 47, 7694 (2008).
23. T. Matsumoto, D. J. Taube, R. A. Periana, H. Taube, H. Yoshida, Anti-Markovnikov Olefin Arylation Catalyzed by an Iridium Complex. *J. Am. Chem. Soc.* 122, 7414 (2000).
24. T. Matsumoto, R. A. Periana, D. J. Taube, H. Yoshida, Regioselective hydrophenylation of olefins catalyzed by an Ir(III) complex. *J. Mol. Catal. A* 180, 1 (2002).
25. J. Oxgaard, R. P. Muller, W. A. Goddard, R. A. Periana, Mechanism of Homogeneous Ir(III) Catalyzed Regioselective Arylation of Olefins. *J. Am. Chem. Soc.* 126, 352 (2004).
26. B. A. McKeown, N. A. Foley, J. P. Lee, T. B. Gunnoe, Hydroarylation of Unactivated Olefins Catalyzed by Platinum(II) Complexes. *Organometallics* 27, 4031 (2008).

27. B. A. McKeown et al., Control of Olefin Hydroarylation Catalysis via a Sterically and Electronically Flexible Platinum(II) Catalyst Scaffold. *Organometallics* 32, 3903 (2013).
28. B. A. McKeown et al., Platinum(II)-catalyzed ethylene hydrophenylation: switching selectivity between alkyl- and vinylbenzene production. *Organometallics* 32, 2857 (2013).
29. P. Hong, H. Yamazaki, Rhodium carbonyl-catalyzed activation of carbon-hydrogen bonds for application in organic synthesis.: V. phenylation of olefins with benzenes. *J. Mol. Catal.* 26, 297 (1984).
30. D. Taube, R. Periana, T. Matsumoto, "Oxidative coupling of olefins and aromatics using a rhodium catalyst and a copper(II) redox agent" (US patent 2000).
31. Y. Fujiwara, I. Noritani, S. Danno, R. Asano, S. Teranishi, Aromatic substitution of olefins. VI. Arylation of olefins with palladium(II) acetate. *J. Am. Chem. Soc.* 91, 7166 (1969).
32. T. Yamada, A. Sakakura, S. Sakaguchi, Y. Obora, Y. Ishii, Oxidative arylation of ethylene with benzene catalyzed by Pd(OAc)$_2$/heteropoly acid/O$_2$ system. *New J. Chem.* 32, 738 (2008).
33. A. Kubota, M. H. Emmert, M. S. Sanford, Pyridine Ligands as Promoters in PdII/0-Catalyzed C—H Olefination Reactions. *Org. Lett.* 14, 1760 (2012).
34. K. Sasaki, T. Sakakura, Y. Tokunaga, K. Wada, M. Tanaka, C=C Double Bond Insertion in Catalytic C—H Activation. Dehydrogenative Cross Coupling of Arenes with Olefins. *Chem. Lett.* 17, 685 (1988).
35. Hoechst Reveals Wacker Process Details. *Chemical & Engineering News Archive* 39, 52 (1961).
36. W in *Catalysis from A to Z*, B. Cornils, W. A. Herrmann, M. Muhler, C.-H. Wong, Eds. (Wiley, 2007), pp. 1511-1524.
37. M. Eckert, G. Fleischmann, R. Jira, H. M. Bolt, K. Golka, Acetaldehyde in *Ullmann's Encyclopedia of Industrial Chemistry*. (Wiley-VCH Verlag GmbH & Co. KGaA, 2000).
38. M. S. Webster-Gardiner et al., Arene C—H activation using Rh(I) catalysts supported by bidentate nitrogen chelates. *Cat. Sci. Tech.* 5, 96 (2015).
39. M. Gómez-Gallego, M. A. Sierra, Kinetic Isotope Effects in the Study of Organometallic Reaction Mechanisms. *Chem. Rev.* 111, 4857 (2011).
40. W. D. Jones, Isotope Effects in C—H Bond Activation Reactions by Transition Metals. *Acc. Chem. Res.* 36, 140 (2003).
41. R. Cramer, Di-μ-chloro-tetrakis(ethene)dirhodium(I). *Inorg. Synth.* 28, 86 (1990).
42. F. Bianchi, M. C. Gallazzi, L. Porri, P. Diversi, Disproportionation of the cyclooctene ligand in the reaction of [IrCl(C$_8$H$_{14}$)$_2$]$_2$. With AgOCOCF$_3$: formation of [Ir(OCOCF$_3$)(C$_8$H$_{14}$)$_2$]$_2$ and [Ir(OCOCF$_3$)(1,5-C$_8$H$_{12}$]$_2$ and their conversion into cationic arene complexes. *J. Organomet. Chem.* 202, 99 (1980).
43. M. M. Khusniyarov, K. Harms, O. Burghaus, J. Sundermeyer, Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino)acenaphthene (BIAN). *Eur. J. Inorg. Chem.* 2006, 2985 (2006).

Example 2

This Example describes the catalytic process that can be used for the conversion of aromatics and olefins to straight-chain vinyl arenes and, hence, through facile hydrogenation straight-chain alkyl arenes. The advantages of this catalyst process over previously reported catalysts at least one or more of the following:
1) oxidants that can be regenerated using oxygen or air
2) efficient conversion of olefin,
3) moderate temperatures (100-250° C.),
4) broad range of pressures for gaseous olefins, and broad range of concentrations for liquid olefins, and
5) formation of truly linear, straight-chain (anti-Markovnikov) allyl, vinyl and alkyl arenes as the major products.

Catalysts employing transition-metals and copper oxidants are combined with the rhodium (I) catalyst and an air recyclable oxidant. In an embodiment, the catalyst includes a simple rhodium (I) salt, either monomeric or multi-nuclear in rhodium, coordinated by anionic salts such as halides, acetates, and the like and/or by neutral ligands such as olefins, carbonyls, phosphines and the like. Similar to those described herein, the Rh(I) catalyst can include [(ethylene)$_2$Rh(μ-TFA)]$_2$), (PPh$_3$)$_3$Rh(Cl), (CO)$_{12}$Rh$_4$ or a rhodium complex of the form L$_2$Rh(L')X, L$_3$RhX, or (L$_1$X$_1$)Rh(L'). In an embodiment, L$_2$ can be comprised of two independent and neutral ligands coordinated to the metal through either nitrogen donors, phosphorus donors, oxygen donors, sulfur donors, and the like, where the donors can take the form of amines, pyridine, phosphines, phosphites, ethers, ketones, imines, and the like; or comprised of a neutral bidentate ligand coordinated to the metal center through either nitrogen donors, phosphorus donors, oxygen donors, sulfur donors, and the like, where the donor can take the form of bipyridines, diimines, bipyrimidine, bisoxazoline diphosphines, phosphinimine, imidates, bispyrazole, bisimidazole, bisphosphorus, and the like; or comprised of a neutral mixed donor ligand including a mixture of the donor groups listed above. In an embodiment, L' can include a neutral ligand coordinated to Rh(I), where the neutral ligand can include olefins, imines, ethers, nitriles, ketones, water, sulfur based ligands, phosphines, and the like. In an embodiment, X can be a mono-anionic, either coordinated to the metal or not, such as, but not limited to, halides, acetates, alkyl groups, aryl groups, and the. In an embodiment, L$_3$ can represent a tridentate ligand coordinated to the metal center in κ$^2$ or κ$^3$ fashion through either nitrogen donors, phosphorus donors, oxygen donors, sulfur donors, or a combination thereof, where the tridentate ligand can include terpyridines, pyridyl diimines, trisphosphine, diphosphine imine, bis(phosphine)pyridine, and the like. In an embodiment, L$_1$X$_1$ can represent a monoanionic bidentate or tridentate ligand coordinated to the metal center in a κ$^2$ or κ$^3$ fashion through either nitrogen donors, phosphorus donors, oxygen donors, sulfur donors, or a combination thereof, where the monoanionic bidentate or tridentate ligand can include diphosphine aryl, imidates, diketiminates, trispyrazolylborate, trisimidazoles, and the like. In an embodiment, the catalyst can be prepared and isolated pure or generated in situ by combination of a Rh(I) salt and appropriate ligand.

A second component of the process can include the oxidant, which can include an air recyclable oxidant such as, but not limited to, copper(II) salts of the form CuX$_2$ (where, for example, X can be, but is not limited to, halide, acetate, trifloroacetate, pivalate, and the like). In addition, oxidants that can be recycled using air or oxygen, such as but not limited to, include iodates, periodates, nitrogen dioxide, can be used. The reactants can include a combination of olefins and arenes, in various amounts, such as, but not limited to, ethylene, propylene, 1-pentene, 1-hexene, isobutylene, vinyl ketones, acrylates, acrylonitriles, etc. and benzene, toluene, naphthalene, halogenated arenes, arenes each optionally with variable functionality such as, but not limited to, ketones, aldehydes, ethers, alkyl, vinyl, nitro, and the like.

In one example of a catalytic reaction, a combination of ($^{FI}$DAB)Rh(TFA)($\eta^2$-C$_2$H$_4$) [$^{FI}$DAB=N,N'-bis(pentafluorophenyl)-2,3-dimethyl-1,4-diaza-1,3-butadiene; TFA=trifluoroacetate] (0.001 mol %), copper(II) acetate (0.012 mol %), ethylene (25 psig), and benzene are heated at 150° C. for 12 hours (eq 1). The product, styrene, is produced with 100% selectivity and with a high yield relative to oxidant (≥95%). The catalyst has been demonstrated to be effective over a broad range of ethylene pressures. This process has been extended to other aromatics, olefins and oxidants, including electron-rich arenes and substituted olefins.

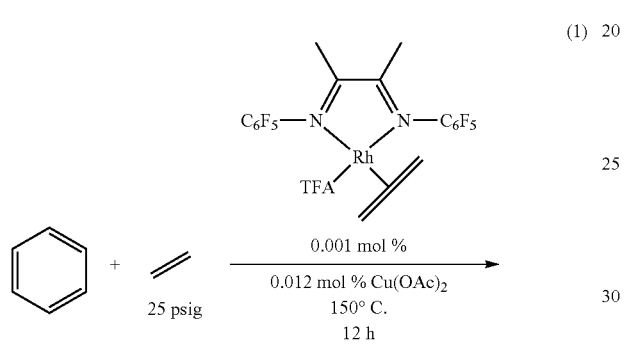

(1)

This type of catalyst has also been shown to catalyze the hydrophenylation of propylene. In another example of a catalytic reaction, a combination of ($^{2tBu}$DAB)Rh(TFA)(NCMe) [$^{2tBu}$DAB=N,N'-bis(2-tertbutylphenyl)-2,3-dimethyl-1,4-diaza-1,3-butadiene] (0.001 mol %), copper(II) acetate (0.024 mol %), propylene (25 psig), and benzene are heated at 180° C. for 24 hours (eq 2). The product mixture consists of linear products (allyl benzene and β-methylstyrene) and branched products (α-methylstyrene) in a 9:1 ratio, while maintaining the high yield (>90%) relative to oxidant. The catalyst has been demonstrated to be effective over a broad range of propylene pressures.

(2)

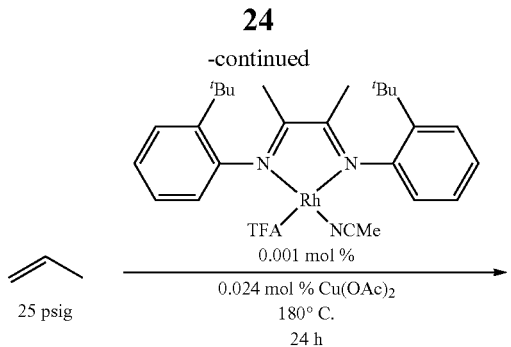

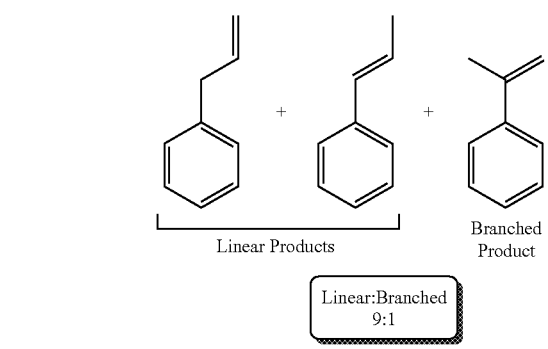

Rhodium(I) complexes supported by tridentate ligands have also been shown to be suitable catalysts for the oxidative hydroarylation of olefins. (NNN)Rh(TFA) [NNN=2,6-diacetylpyridine-bis(2,6-diisopropylaniline)] (0.001 mol %), copper(II) acetate (0.024 mol %), propylene (25 psig), and benzene are heated at 180° C. for 24 hours (eq 3). The product mixture consists of linear products (allyl benzene, and cis- and trans-β-methylstyrene) and branched products (α-methylstyrene) in a 10:1 ratio.

(3)

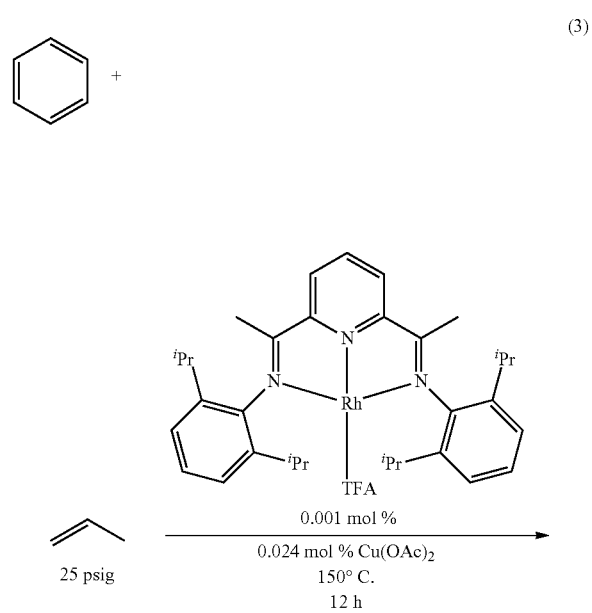

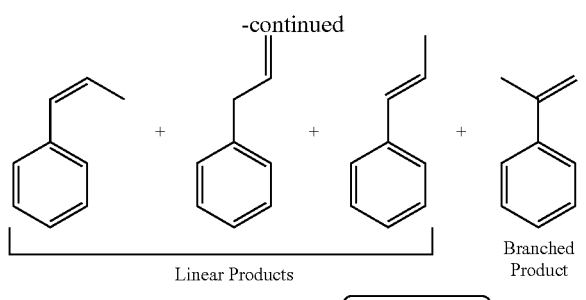

Complexes with formally mono-anionic ancillary ligands are also effective catalyst for this transformation. A combination of $(^{FI}NacNac)Rh(\eta^2-C_2H_4)_2$ [$^{FI}NacNac$=N,N'-bis(pentafluorophenyl)-1,3-diketimine] (0.001 mol %), copper (II) acetate (0.012 mol %), ethylene (25 psig), and benzene are heated at 150° C. for 24 hours (eq 1). The product, styrene, is produced with 100% selectivity and with a high yield (≥95%).

(4)

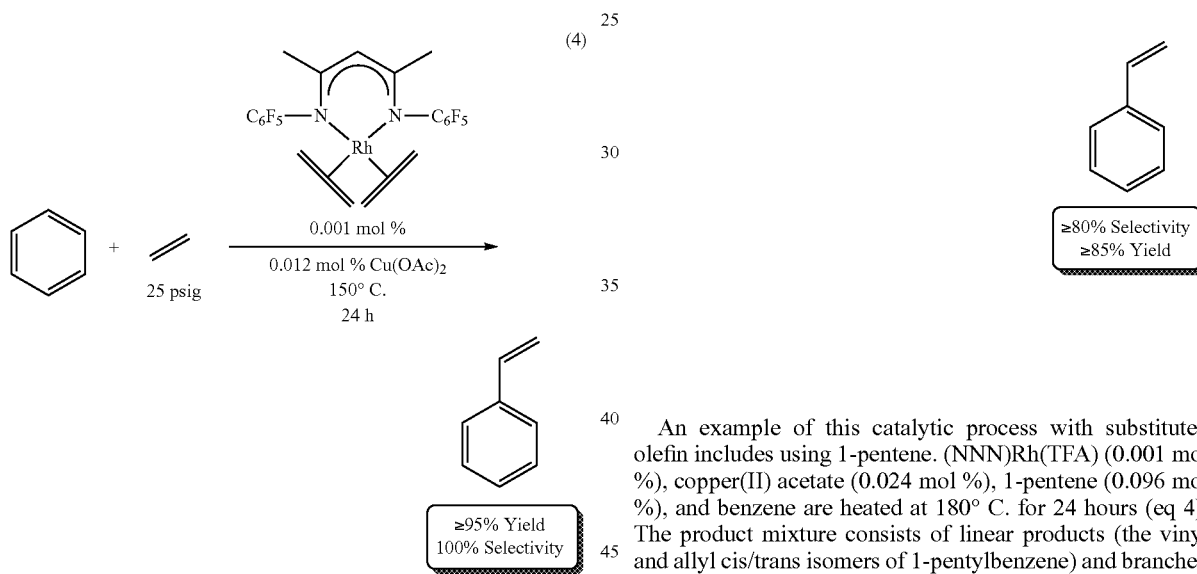

The Rh(I) catalysts can also be generated easily in situ. Combining $[(C_2H_4)_2Rh(\mu-Cl)]_2$ (0.001 mol %) with 0.002 mol % ancillary ligand (diimines, diketiminates, tridentate ligands, etc.) in benzene forms the catalyst precursor. Subsequent addition of copper(II) acetate (0.024 mol %) and pressurization with ethylene (25 psig) allows for a catalytic run upon heating to between 120-200° C. for 12 hours (eq 5). The product, styrene, is produced with greater than 80% selectivity and with a high yield relative to oxidant (≥85%).

(5)

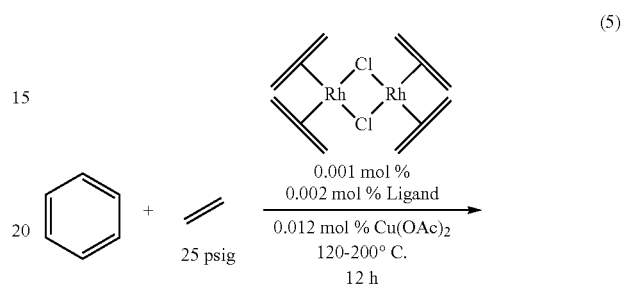

An example of this catalytic process with substituted olefin includes using 1-pentene. (NNN)Rh(TFA) (0.001 mol %), copper(II) acetate (0.024 mol %), 1-pentene (0.096 mol %), and benzene are heated at 180° C. for 24 hours (eq 4). The product mixture consists of linear products (the vinyl and allyl cis/trans isomers of 1-pentylbenzene) and branched products (vinyl isomers of 2-pentylbenzene and 3-pentylbenzene).

(6)

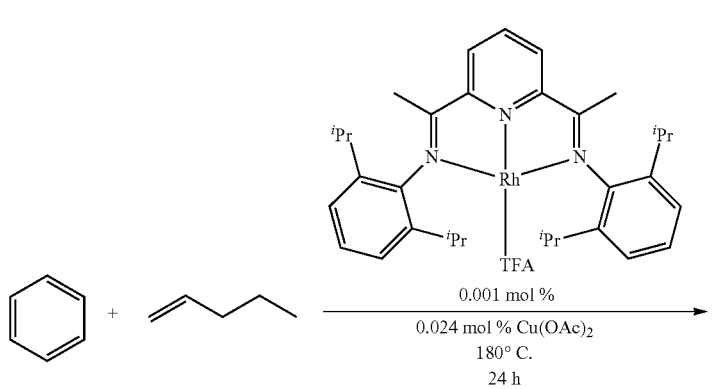

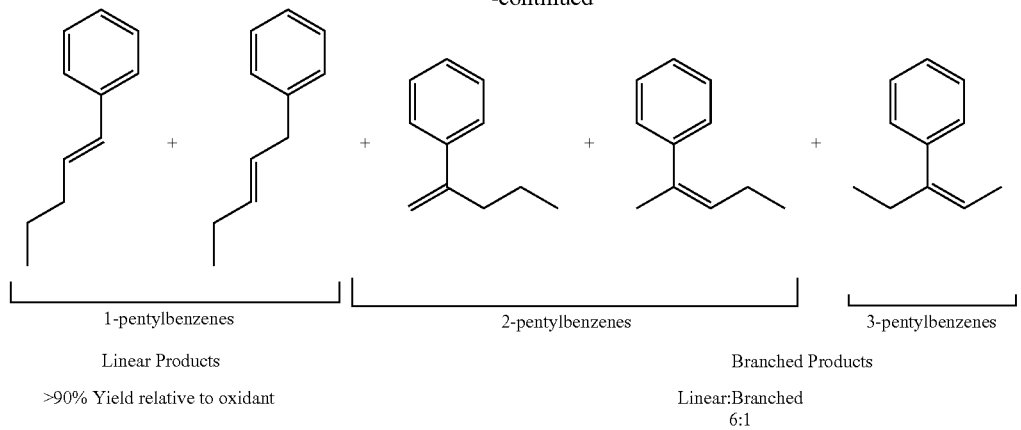

1-pentylbenzenes — Linear Products — >90% Yield relative to oxidant 2-pentylbenzenes — Branched Products — Linear:Branched 6:1

3-pentylbenzenes

Rhodium(I) complexes supported by chelating ligands with a combination of nitrogen and phosphorus based ligands have been shown to be suitable catalysts for the oxidative hydroarylation of olefins. For example, (PNP)Rh(Cl) [PNP=2,6-bis((dicyclohexylphosphine)methyl)pyridine)] (0.001 mol %), copper(II) acetate (0.024 mol %), propylene (25 psig) and benzene are heated at 180° C. for 24 hours (eq 7). The product mixture consists of linear products (allyl benzene, and cis- and trans-β-methylstyrene) and branched products (α-methylstyrene) in a 8:1 ratio.

An example of disubstituted olefins is given by utilizing isobutylene. (PNP)Rh(Cl) [PNP=2,6-bis((dicyclohexylphosphanyl)methyl)pyridine)] (0.001 mol %), copper(II) acetate (0.024 mol %), isobutylene (25 psig), and benzene are heated at 180° C. for 20 hours (eq 8). The product mixture consists of linear products [(2-methylallyl benzene, and (2-methylprop-1-ene-1-yl)benzene] and trace quantities of branched products [(2-methyl-prop-1-en-2-yl)benzene].

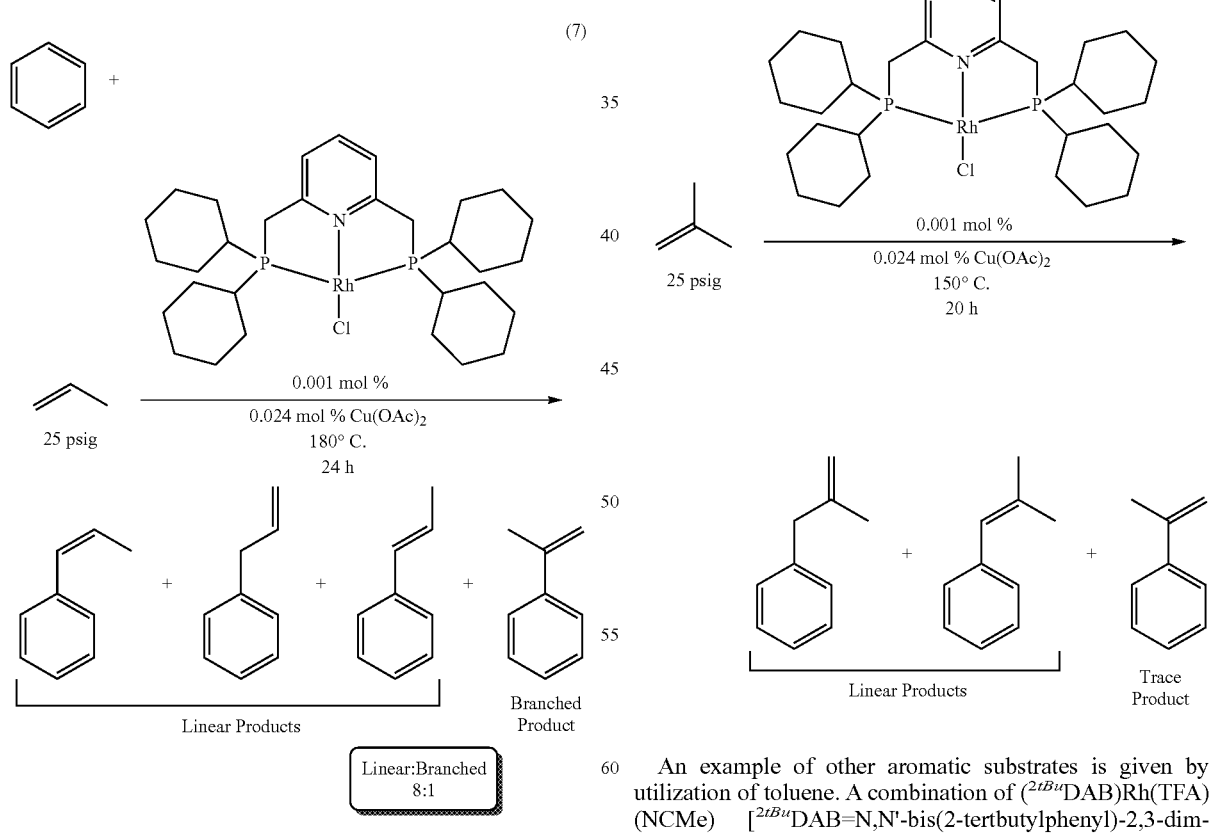

An example of other aromatic substrates is given by utilization of toluene. A combination of ($^{2tBu}$DAB)Rh(TFA)(NCMe) [$^{2tBu}$DAB=N,N'-bis(2-tertbutylphenyl)-2,3-dimethyl-1,4-diaza-1,3-butadiene] (0.001 mol %), copper(II) acetate (0.024 mol %), ethylene (40 psig), and toluene are heated at 180° C. for 24 hours (eq 9). The product mixture consists of ortho:meta:para isomers in a 1:3.5:3.5 ratio, while maintaining the high yield (>90%) relative to oxidant.

(9)

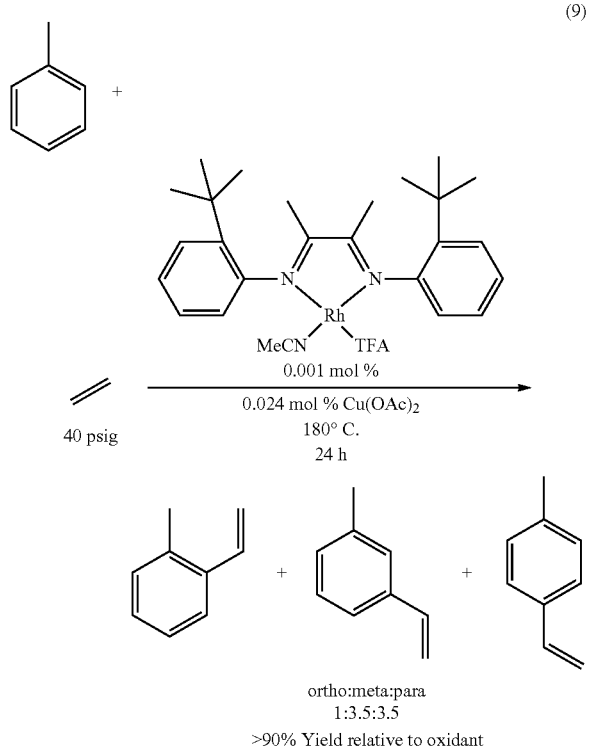

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A method of making a substituted arene, comprising reacting an arene and olefin with a catalyst and an oxidant, with the proviso that the method is performed in the absence of CO, wherein the catalyst is:

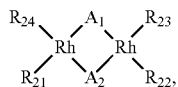

wherein $A_1$ and $A_2$ are independently selected from the group consisting of a halogen and an acetate group; and $R_{21}$, $R_{22}$, $R_{23}$, and $R_{24}$ are each independently selected from an olefin:

wherein the oxidant is a copper(II) salt, iodate, periodate, nitrogen dioxide, silver salt, peroxide, dioxygen, air, or a combination thereof;

wherein the arene is benzene or naphthalene, wherein the arene is optionally substituted with 1-4 substituents selected from the group consisting of halo, methyl, carboxylate, nitro, and alkoxy;

wherein the olefin is:

and

R is hydrogen, a halide, an alkyl, an alkenyl, a carbocycle group, a heterocyclo, an aryl, or a heteroaryl;

to form a product, wherein the product is

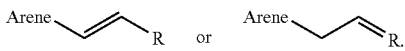

2. The method of claim 1, wherein the reacting is at a reaction temperature of 100° C. to 300° C.

3. The method of claim 2, wherein the reaction temperature is 100° C. to 250° C.

4. The method of claim 1, further comprising:
reacting the product with a second catalyst in the presence of $H_2$, wherein the second catalyst is selected from the group consisting of: Pt/C, Pd/C, Raney Ni, Wilkinson's Catalyst, and $PtO_2$.

5. The method of claim 1, wherein the arene is selected from the group consisting of benzene, naphthalene, toluene, xylene, mesitylene, chlorobenzene, fluorobenzene, bromobenzene, iodobenzene, dichlorobenzene, difluorobenzene, or dibromobenzene.

6. The method of claim 1, wherein the arene is benzene, naphthalene, or toluene.

7. The method of claim 1, wherein the olefin is ethylene, propylene, pentene, hexene, or isobutylene.

8. The method of claim 1, wherein the arene and olefin are present in a molar ratio of arene to olefin of 1:100 to 1000:1.

9. The method of claim 1, wherein the catalyst is present in an amount of 5 mol % to 0.00001 mol % relative to arene.

10. The method of claim 1, wherein the olefin is a gaseous olefin at a pressure of 10 psig to 5000 psig.

11. The method of claim 1, wherein the olefin is a gaseous olefin at a pressure of 10 psig to 90 psig.

* * * * *